(12) United States Patent
Scheller et al.

(10) Patent No.: US 9,132,035 B2
(45) Date of Patent: *Sep. 15, 2015

(54) STEERABLE LASER PROBE

(71) Applicant: Katalyst Surgical, LLC, Chesterfield, MO (US)

(72) Inventors: Gregg D Scheller, Wildwood, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/604,824

(22) Filed: Jan. 26, 2015

(65) Prior Publication Data

US 2015/0141970 A1   May 21, 2015

Related U.S. Application Data

(63) Continuation of application No. 13/684,217, filed on Nov. 22, 2012, now Pat. No. 8,968,277.

(51) Int. Cl.
| | |
|---|---|
| *A61B 18/18* | (2006.01) |
| *A61B 17/00* | (2006.01) |
| *A61F 9/008* | (2006.01) |
| *A61B 19/00* | (2006.01) |

(52) U.S. Cl.
CPC .............. *A61F 9/008* (2013.01); *A61F 9/00821* (2013.01); *A61B 19/22* (2013.01); *A61B 19/2203* (2013.01); *A61B 2019/2242* (2013.01); *A61F 2009/00863* (2013.01); *A61F 2009/00872* (2013.01); *A61F 2250/0006* (2013.01)

(58) Field of Classification Search
CPC .............. A61B 19/22; A61B 19/2203; A61B 2019/2242; A61F 9/008; A61F 2009/00872; A61F 9/00821; A61F 2009/00863
USPC ......................................................... 606/1, 4
See application file for complete search history.

(56) References Cited

U.S. PATENT DOCUMENTS

| | | | |
|---|---|---|---|
| 5,190,050 A | | 3/1993 | Nitzsche |
| 5,355,871 A | * | 10/1994 | Hurley et al. ................. 606/170 |
| 5,381,782 A | | 1/1995 | DeLaRama et al. |
| 5,439,000 A | | 8/1995 | Gunderson et al. |

(Continued)

FOREIGN PATENT DOCUMENTS

| | | |
|---|---|---|
| EP | 0900547 B1 | 3/1999 |
| WO | WO 2006/091597 A1 | 8/2006 |

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.

*Primary Examiner* — Lynsey Crandall
*Assistant Examiner* — Sebastian X Lukjan
(74) *Attorney, Agent, or Firm* — Kevin P. Rollins

(57) ABSTRACT

A steerable laser probe may include a handle, an actuation mechanism of the handle, an optic fiber, and a housing tube. The housing tube may include a first housing tube portion having a first stiffness and a second housing tube portion having a second stiffness. The second stiffness may be greater than the first stiffness. The optic fiber may be disposed within the housing tube and within an inner bore of the handle. A portion of the optic fiber may be fixed to an inner portion of the housing tube.

20 Claims, 34 Drawing Sheets

(56) References Cited

U.S. PATENT DOCUMENTS

| | | |
|---|---|---|
| 5,454,794 A | 10/1995 | Narciso et al. |
| 5,520,222 A | 5/1996 | Chikama |
| 6,123,699 A | 9/2000 | Webster, Jr. |
| 6,126,654 A | 10/2000 | Giba et al. |
| 6,198,974 B1 | 3/2001 | Webster, Jr. |
| 6,488,695 B1 | 12/2002 | Hickingbotham |
| 6,505,530 B2 | 1/2003 | Adler et al. |
| 6,530,913 B1 | 3/2003 | Giba et al. |
| 6,551,302 B1 | 4/2003 | Rosinko et al. |
| 6,572,608 B1 | 6/2003 | Lee et al. |
| 6,620,153 B2 | 9/2003 | Mueller et al. |
| 6,730,076 B2 | 5/2004 | Hickingbotham |
| 6,863,668 B2 | 3/2005 | Gillespie et al. |
| 6,984,230 B2 | 1/2006 | Scheller et al. |
| 7,004,957 B1 | 2/2006 | Dampney et al. |
| 7,303,533 B2 | 12/2007 | Johansen et al. |
| 7,402,158 B2 | 7/2008 | Scheller et al. |
| 7,632,242 B2 | 12/2009 | Griffin et al. |
| 7,766,904 B2 | 8/2010 | McGowan, Sr. et al. |
| 8,038,692 B2 | 10/2011 | Valencia et al. |
| 8,075,553 B2 | 12/2011 | Scheller et al. |
| 8,197,468 B2 | 6/2012 | Scheller et al. |
| 2003/0171762 A1 | 9/2003 | Forchette et al. |
| 2004/0181138 A1 | 9/2004 | Hindricks et al. |
| 2004/0249367 A1 | 12/2004 | Saadat et al. |
| 2005/0054900 A1 | 3/2005 | Mawn et al. |
| 2005/0154379 A1* | 7/2005 | McGowan et al. ............... 606/4 |
| 2005/0157985 A1 | 7/2005 | McGowan, Sr. et al. |
| 2005/0272975 A1 | 12/2005 | McWeeny et al. |
| 2007/0185514 A1 | 8/2007 | Kirchhevel |
| 2008/0188910 A1* | 8/2008 | Spaide ............................ 607/89 |
| 2009/0018393 A1 | 1/2009 | Dick et al. |
| 2009/0187170 A1 | 7/2009 | Auld et al. |
| 2009/0312750 A1 | 12/2009 | Spaide |
| 2010/0004642 A1 | 1/2010 | Lumpkin |
| 2010/0268234 A1 | 10/2010 | Aho et al. |
| 2011/0028947 A1 | 2/2011 | Scheller et al. |
| 2012/0116361 A1 | 5/2012 | Hanlon et al. |
| 2013/0035551 A1 | 2/2013 | Yu et al. |
| 2013/0060240 A1 | 3/2013 | Scheller et al. |
| 2013/0071507 A1 | 3/2013 | Scheller et al. |
| 2013/0096541 A1 | 4/2013 | Scheller et al. |
| 2013/0116671 A1 | 5/2013 | Scheller et al. |
| 2013/0150838 A1 | 6/2013 | Scheller et al. |
| 2013/0165910 A1 | 6/2013 | Scheller et al. |
| 2013/0261610 A1 | 10/2013 | LaConte et al. |

* cited by examiner

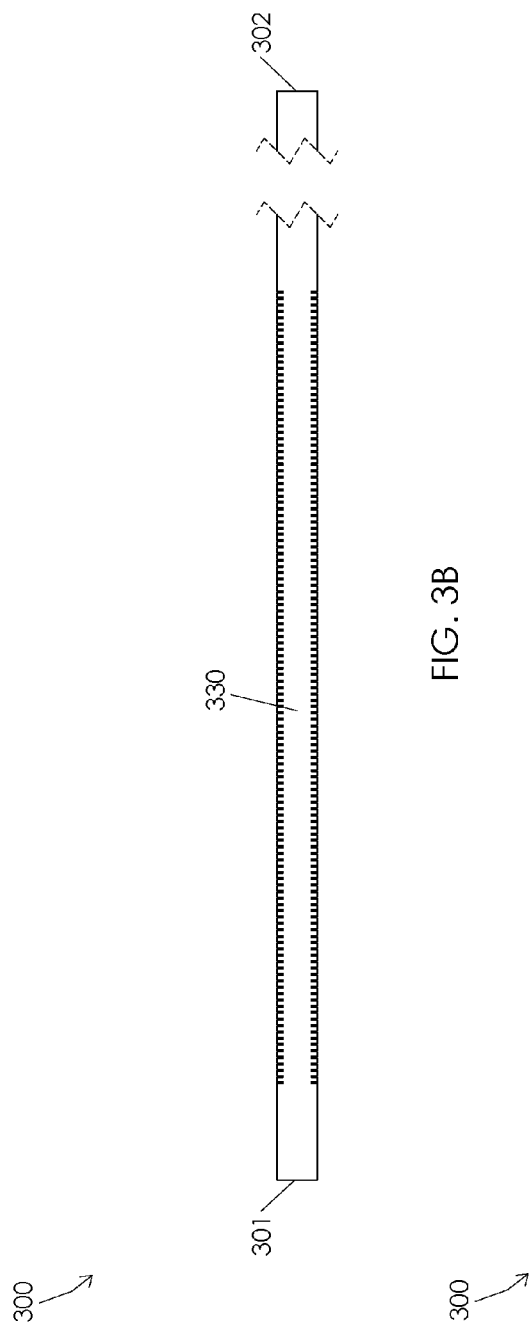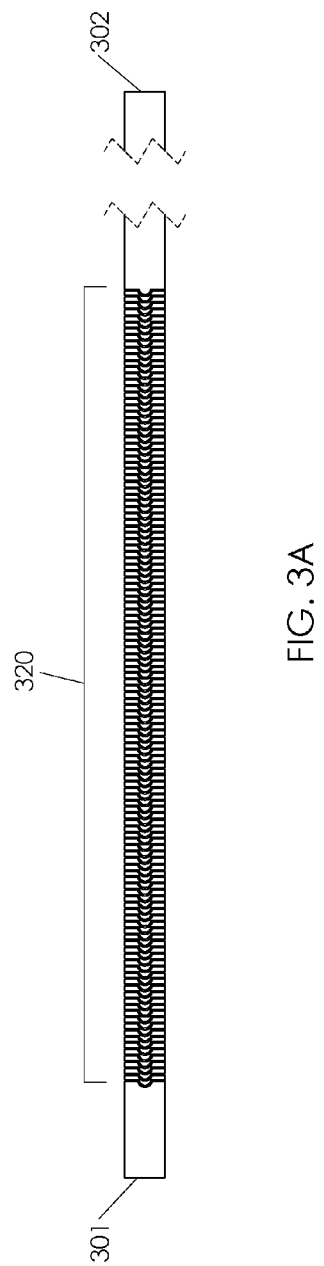

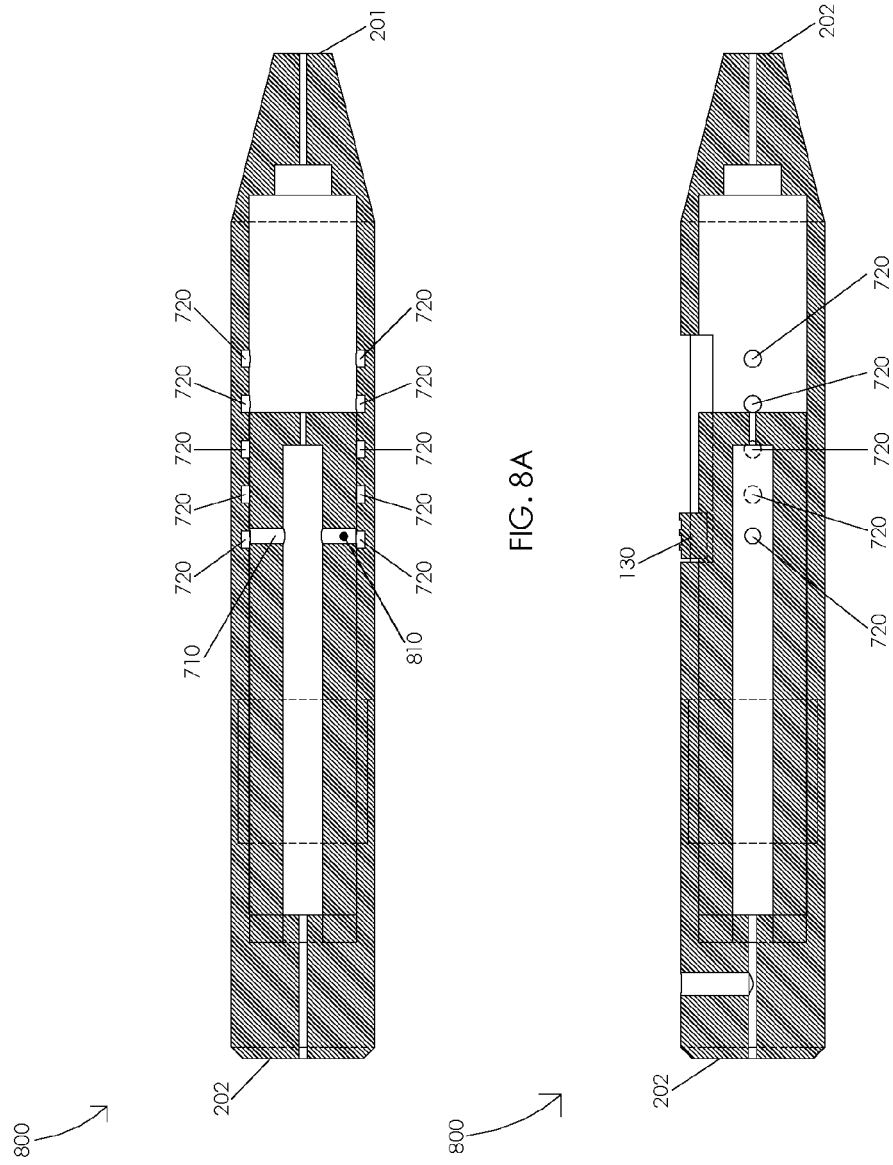

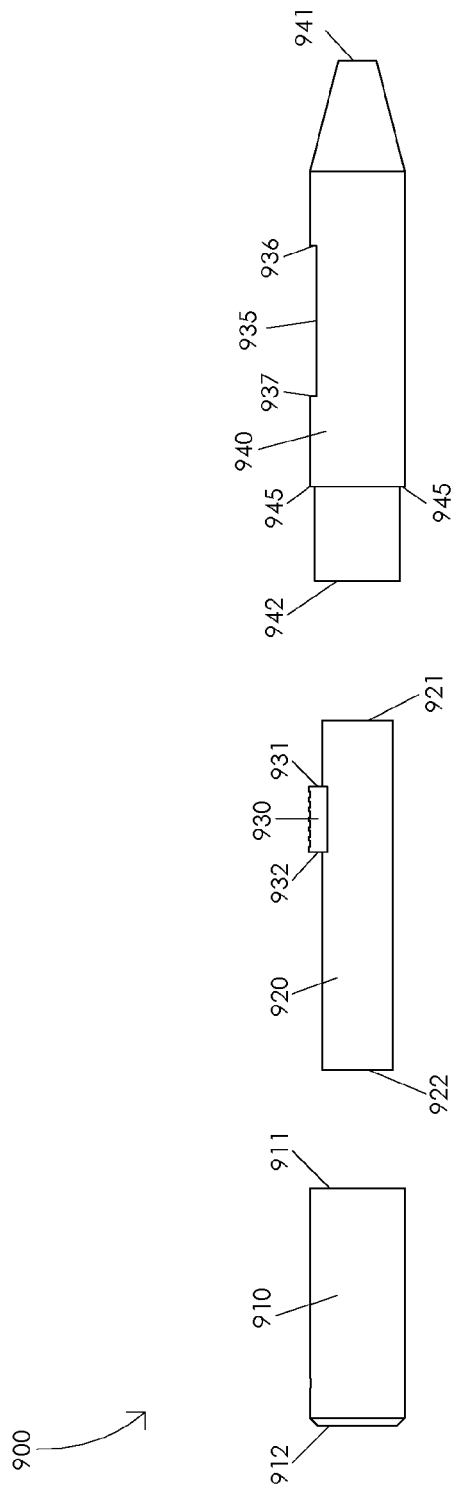
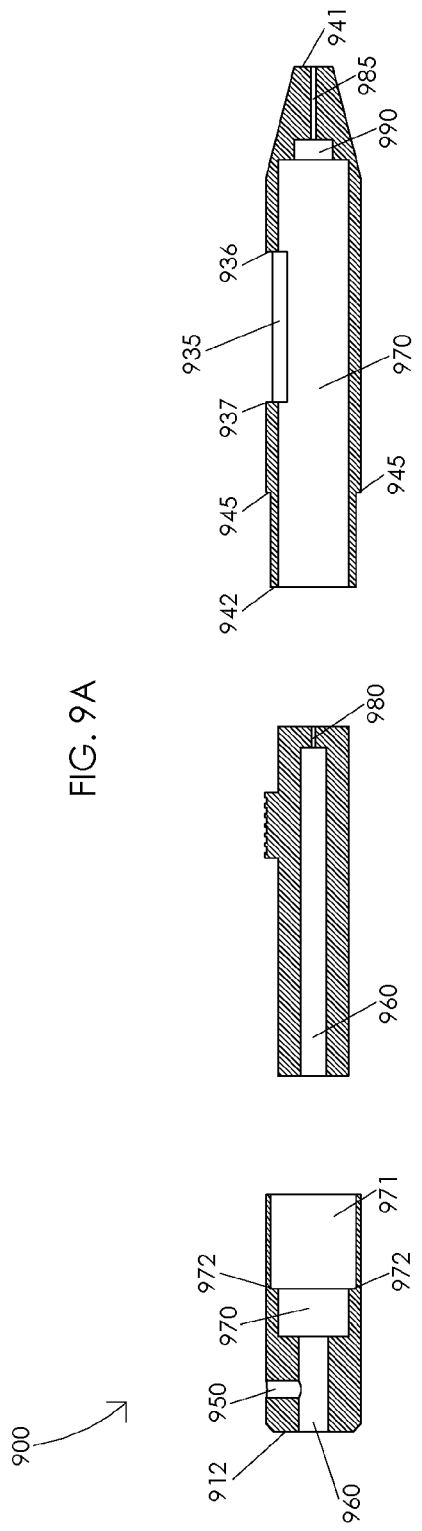
FIG. 9A
FIG. 9B

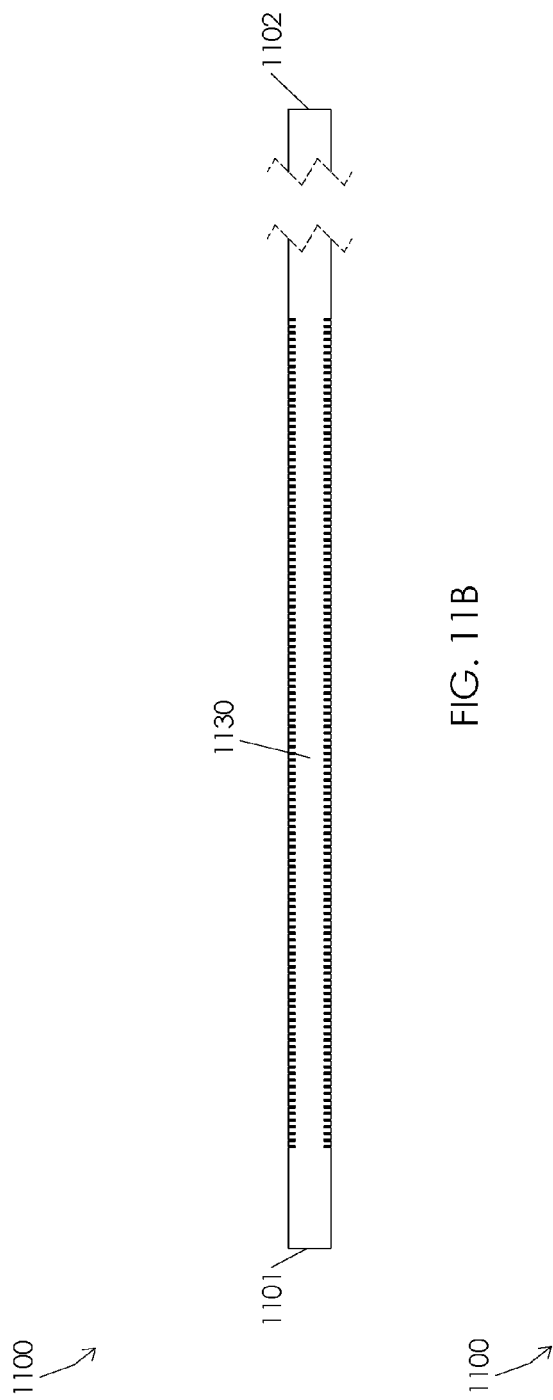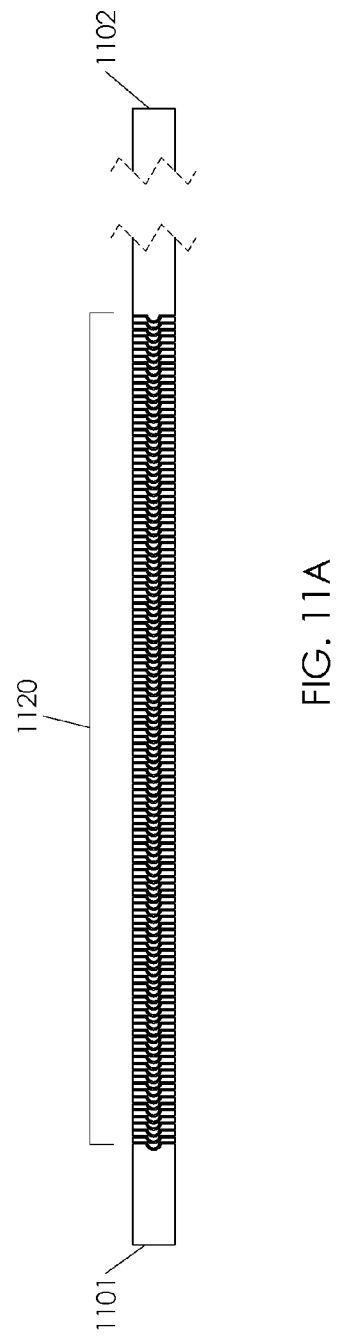

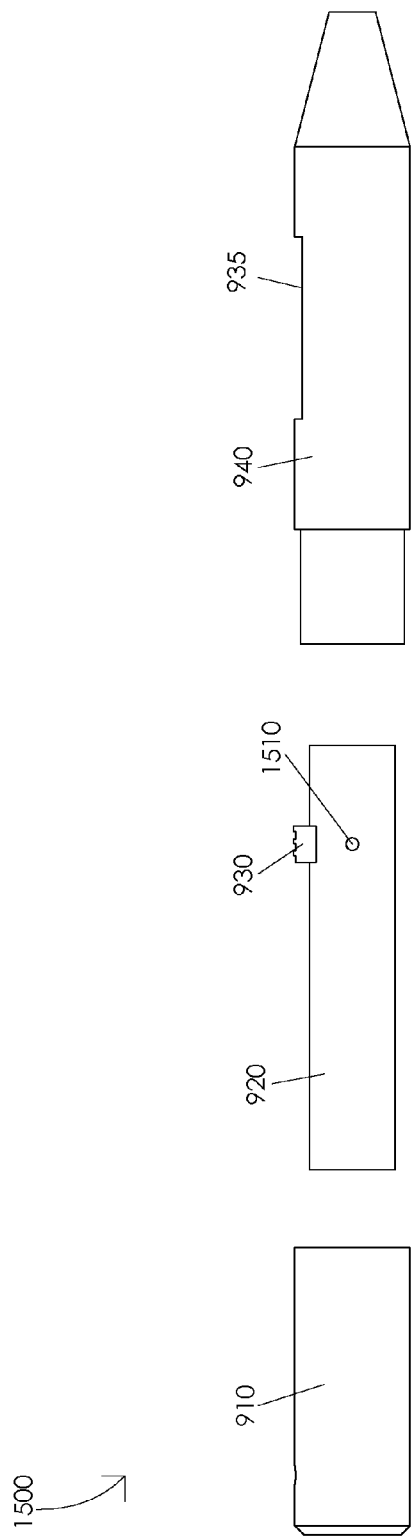
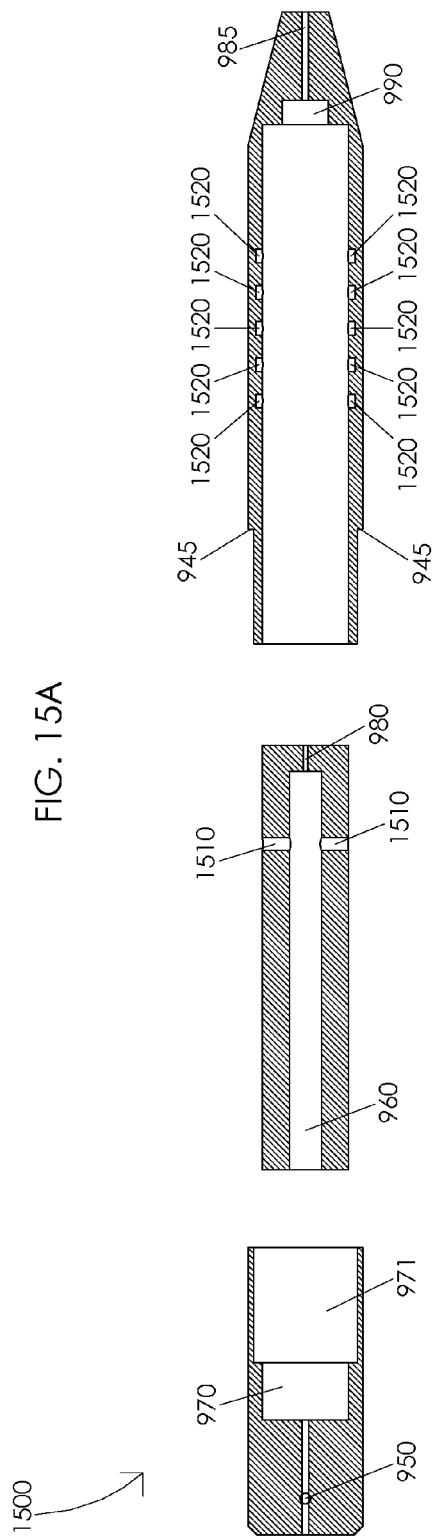
FIG. 15A
FIG. 15B

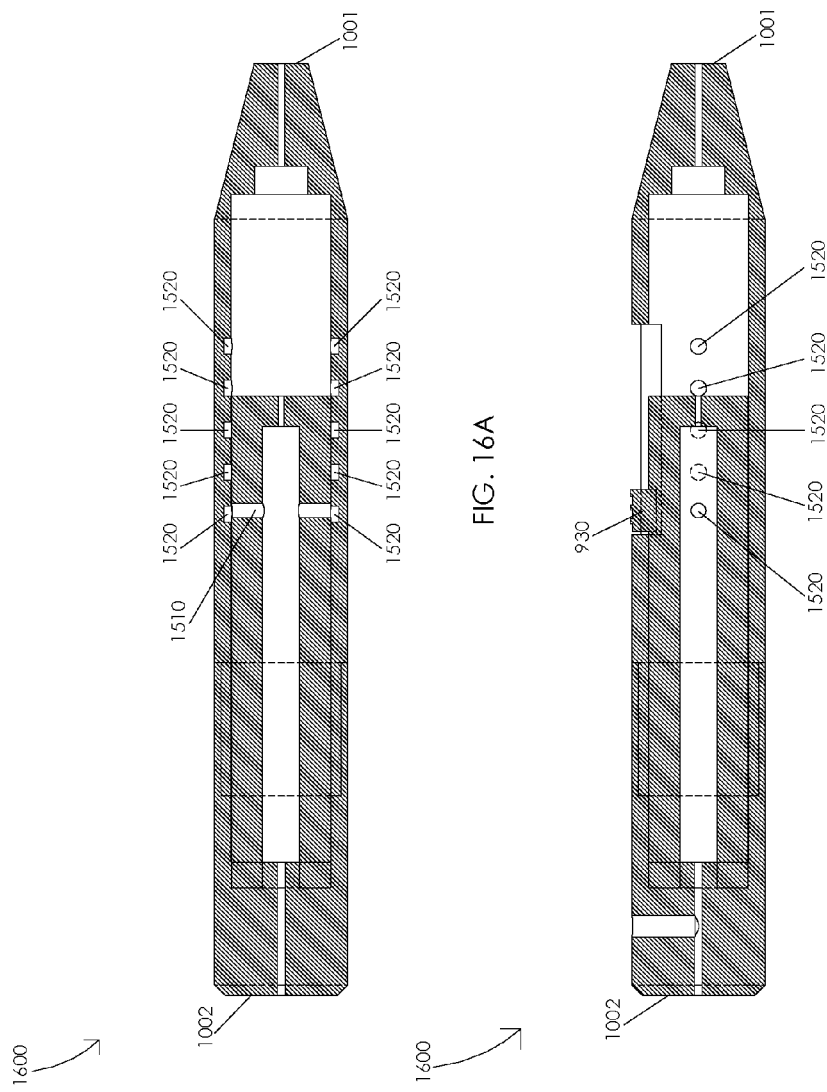

STEERABLE LASER PROBE

CROSS-REFERENCE TO RELATED APPLICATIONS

This application is a continuation of prior application Ser. No. 13/684,217, filed Nov. 22, 2012.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure provides a steerable laser probe. In one or more embodiments, a steerable laser probe may comprise a handle, an actuation mechanism of the handle, an optic fiber, and a housing tube. Illustratively, the housing tube may comprise a first housing tube portion having a first stiffness and a second housing tube portion having a second stiffness. In one or more embodiments, the second stiffness may be greater than the first stiffness. Illustratively, the optic fiber may be disposed within the housing tube and within an inner bore of the handle. In one or more embodiments, a portion of the optic fiber may be fixed to an inner portion of the housing tube, e.g., by a biocompatible adhesive or any other suitable means.

Illustratively, an actuation of the actuation mechanism may be configured to gradually compress a first housing tube portion of the housing tube. In one or more embodiments, a compression of the first housing tube portion may be configured to gradually curve the housing tube. Illustratively, a gradual curving of the housing tube may be configured to gradually curve the optic fiber.

In one or more embodiments, an actuation of the actuation mechanism may be configured to gradually decompress a first housing tube portion of the housing tube. Illustratively, a decompression of the first housing tube portion may be configured to gradually straighten the housing tube. In one or more embodiments, a gradual straightening of the housing tube may be configured to gradually straighten the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 3A, 3B, and 3C are schematic diagrams illustrating a housing tube;

FIGS. 8A and 8B are schematic diagrams illustrating a handle;

FIGS. 9A and 9B are schematic diagrams illustrating an exploded view of a handle assembly;

FIGS. 11A, 11B, and 11C are schematic diagrams illustrating a housing tube;

FIGS. 15A and 15B are schematic diagrams illustrating an exploded view of a handle assembly;

FIGS. 16A and 16B are schematic diagrams illustrating a handle.

DETAILED DESCRIPTION OF AN ILLUSTRATIVE EMBODIMENT

Figure 1A:
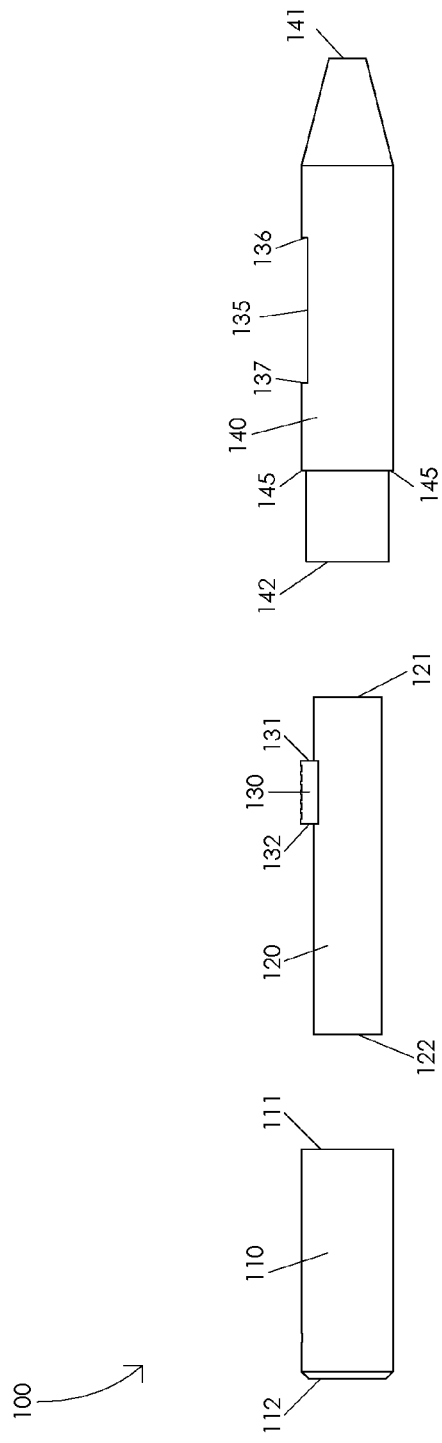
FIGS. 1A and 1B are schematic diagrams illustrating an exploded view of a handle assembly.
Figure 1B:
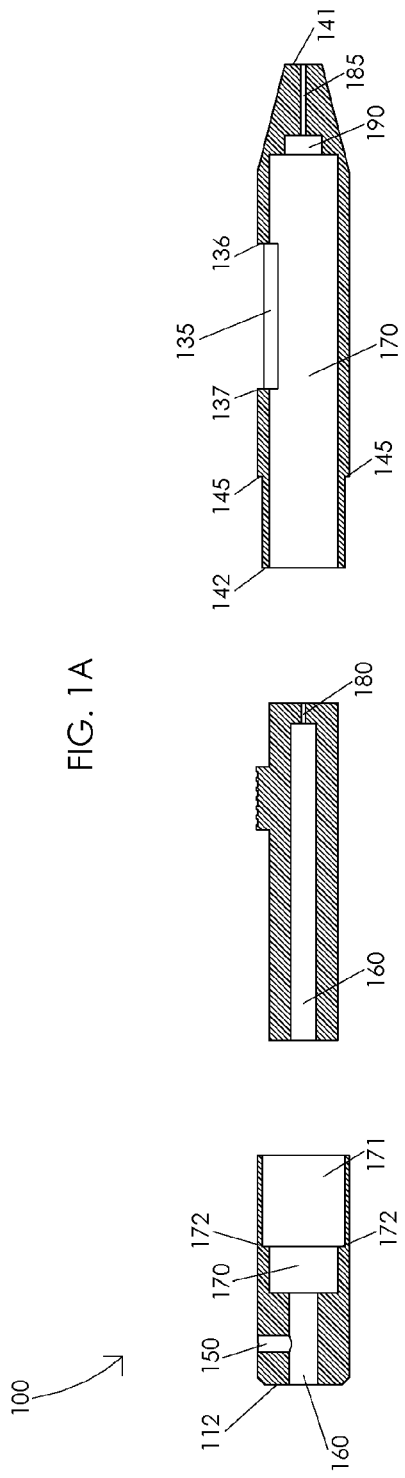

FIGS. 1A and 1B are schematic diagrams illustrating an exploded view of a handle assembly 100. FIG. 1A illustrates a side view of a handle assembly 100. In one or more embodiments, a handle assembly 100 may comprise an outer cylinder 110 having an outer cylinder distal end 111 and an outer cylinder proximal end 112, an actuation mechanism 120 having an actuation mechanism distal end 121 and an actuation mechanism proximal end 122, and a handle base 140 having a handle base distal end 141 and a handle base proximal end 142. Illustratively, actuation mechanism 120 may comprise an actuation control 130. In one or more embodiments, actuation control 130 may comprise an actuation control distal end 131 and an actuation control proximal end 132. Illustratively, handle base 140 may comprise an actuation channel 135 having an actuation channel distal end 136 and an actuation channel proximal end 137. In one or more embodiments, handle base 140 may comprise an outer cylinder interface 145. Illustratively, outer cylinder interface 145 may be configured to interface with outer cylinder 110, e.g., outer cylinder interface 145 may be configured to interface with outer cylinder distal end 111. FIG. 1B illustrates a cross-sectional view of a handle assembly 100. In one or more embodiments, a handle assembly 100 may comprise a fixation mechanism housing 150, an inner bore 160, an actuation mechanism guide 170, a handle base housing 171, a housing tube housing 180, a housing tube guide 185, and a pressure mechanism housing 190. Illustratively, handle base housing 171 may comprise a handle base interface 172. Outer cylinder 110, actuation mechanism 120, and handle base 140 may be manufactured from any suitable material, e.g., polymers, metals, metal alloys, etc., or from any combination of suitable materials.

Figure 2A:
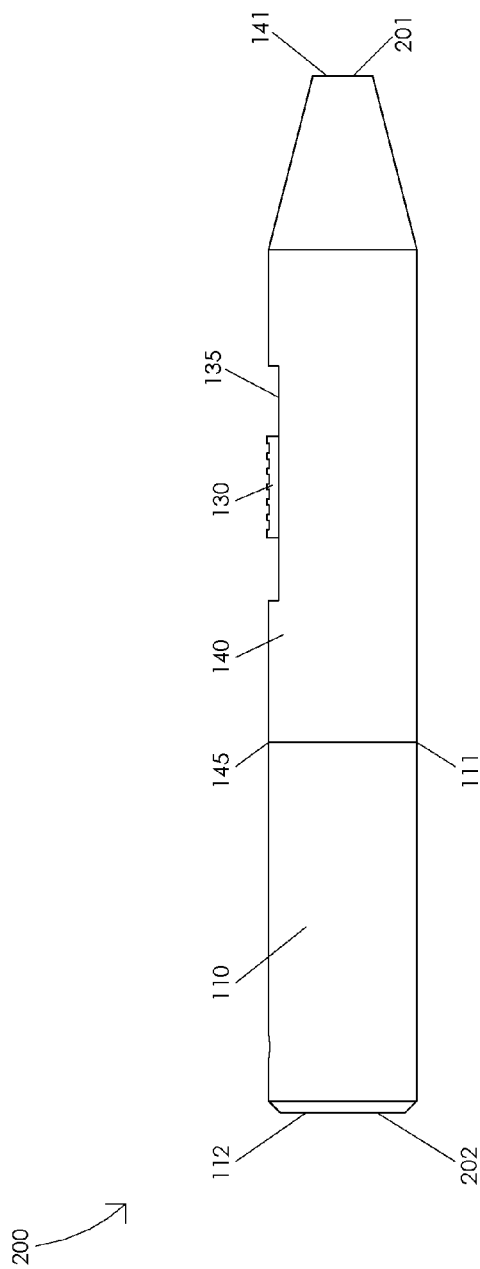
FIGS. 2A and 2B are schematic diagrams illustrating a handle.
Figure 2B:
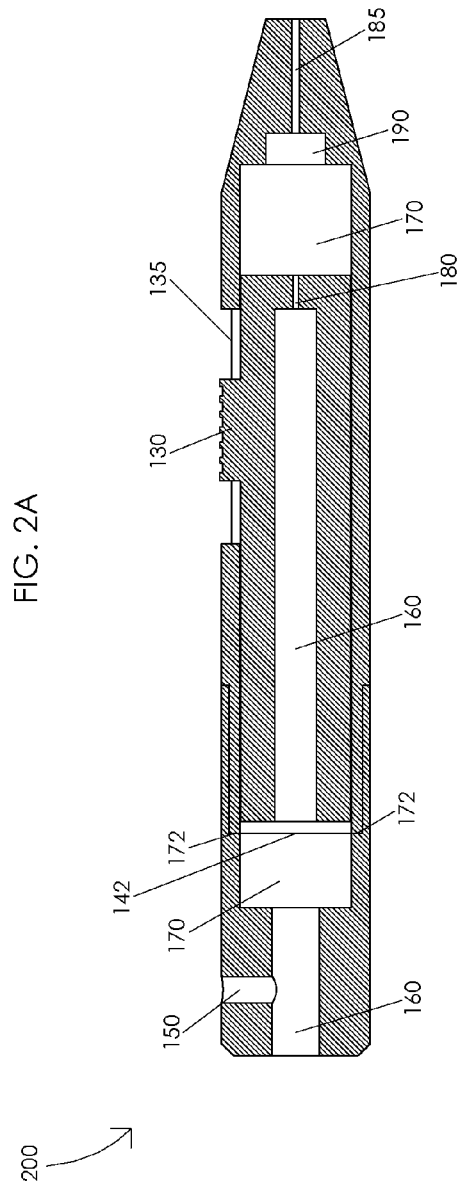

FIGS. 2A and 2B are schematic diagrams illustrating a handle 200. FIG. 2A illustrates a side view of a handle 200. In one or more embodiments, handle 200 may comprise a handle distal end 201 and a handle proximal end 202. Illustratively, handle distal end 201 may comprise handle base distal end 141. In one or more embodiments, handle proximal end 202 may comprise outer cylinder proximal end 112. Illustratively, outer cylinder distal end 111 may be disposed adjacent to outer cylinder interface 145. In one or more embodiments, actuation control 130 may be disposed with actuation channel 135.

FIG. 2B illustrates a cross-sectional view of a handle 200. In one or more embodiments, a portion of handle base 140 may be disposed within a portion of outer cylinder 110. Illustratively, a portion of handle base 140 may be disposed within handle base housing 171. In one or more embodiments, a portion of handle base 140 may be disposed within handle base housing 171 wherein handle base proximal end 142 may be disposed adjacent to handle base interface 172. Illustratively, actuation mechanism 120 may be disposed within actuation mechanism guide 170. In one or more embodiments, actuation mechanism 120 may be configured to actuate within actuation mechanism guide 170. Illustratively, actuation control 130 may be configured to control an actuation of actuation mechanism 120, e.g., within actuation mechanism guide 170.

In one or more embodiments, an actuation of actuation control 130 within actuation channel 135 may be configured to actuate actuation mechanism 120 within actuation mechanism guide 170. Illustratively, an actuation of actuation control distal end 131 towards actuation channel distal end 136 may be configured to actuate actuation mechanism distal end 121 towards handle distal end 201. In one or more embodiments, an actuation of actuation control proximal end 132 towards actuation channel proximal end 137 may be configured to actuate actuation mechanism proximal end 122 towards handle proximal end 202. Illustratively, a pressure mechanism, e.g., a spring, may be disposed within pressure mechanism housing 190. In one or more embodiments, a pressure mechanism may be configured to resist an actuation of actuation mechanism distal end 121 towards handle distal end 201. Illustratively, a pressure mechanism may be configured to facilitate an actuation of actuation mechanism proximal end 122 towards handle proximal end 202.

Figure 3C:
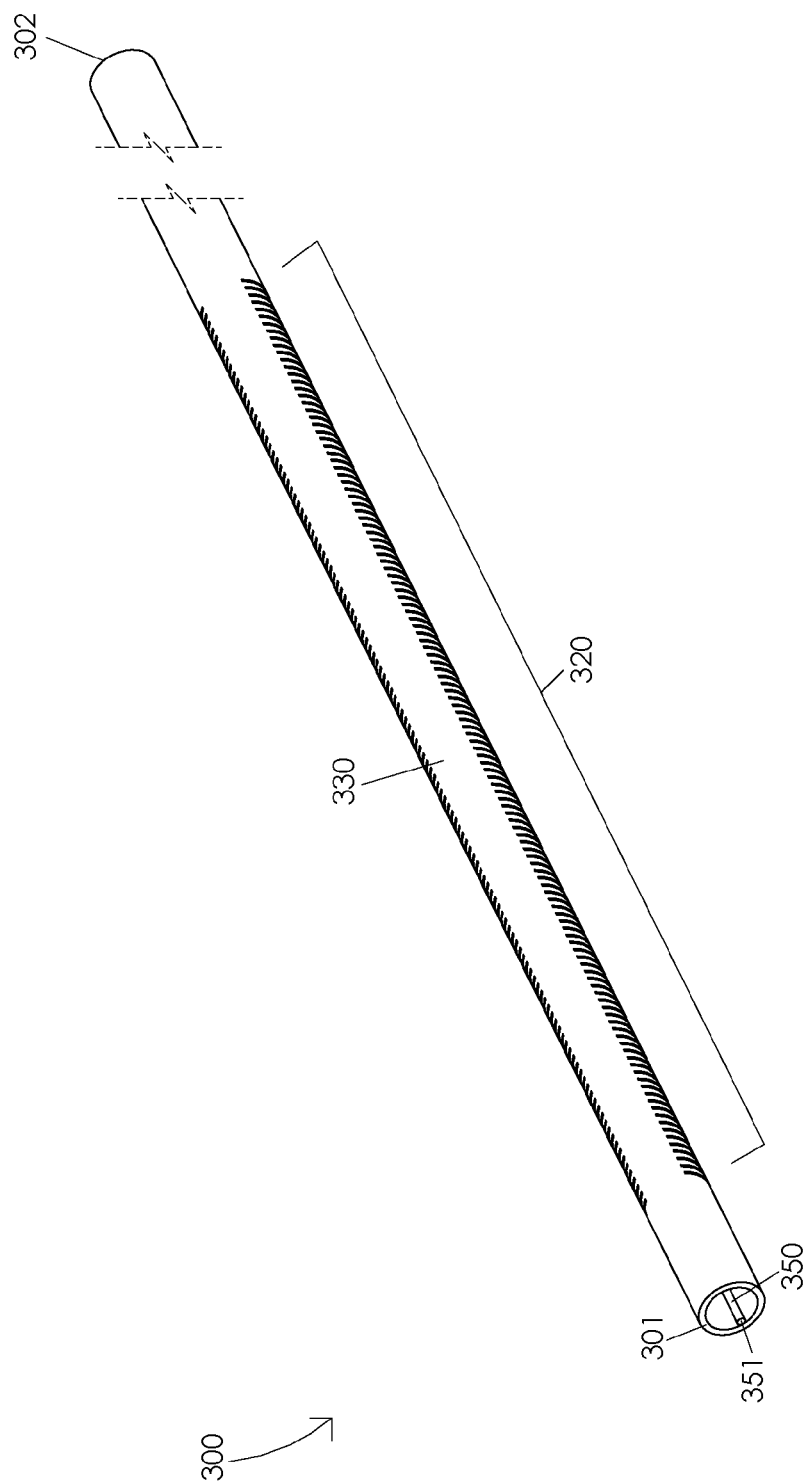

FIGS. 3A, 3B, and 3C are schematic diagrams illustrating a housing tube 300. In one or more embodiments, housing tube 300 may comprise a housing tube distal end 301 and a housing tube proximal end 302. Housing tube 300 may be manufactured from any suitable material, e.g., polymers, metals, metal alloys, etc., or from any combination of suitable materials. FIG. 3A illustrates a housing tube 300 oriented to illustrate a first housing tube portion 320. Illustratively, first housing tube portion 320 may have a first stiffness. FIG. 3B illustrates a housing tube 300 oriented to illustrate a second housing tube portion 330. Illustratively, second housing tube portion 330 may have a second stiffness. In one or more embodiments, the second stiffness may be greater than the first stiffness. Illustratively, first housing tube portion 320 may comprise a first material having a first stiffness. In one or more embodiments, second housing tube portion 330 may comprise a second material having a second stiffness. Illustratively, the second stiffness may be greater than the first stiffness.

In one or more embodiments, housing tube 300 may comprise a non-uniform inner diameter or a non-uniform outer diameter, e.g., to vary a stiffness of one or more portions of housing tube 300. Illustratively, a first housing tube portion 320 may comprise a first inner diameter of housing tube 300 and a second housing tube portion 330 may comprise a second inner diameter of housing tube 300. In one or more embodiments, the first inner diameter of housing tube 300 may be larger than the second inner diameter of housing tube 300. Illustratively, a first housing tube portion 320 may comprise a first outer diameter of housing tube 300 and a second housing tube portion 330 may comprise a second outer diameter of housing tube 300. In one or more embodiments, the first outer diameter of housing tube 300 may be smaller than the second outer diameter of housing tube 300.

In one or more embodiments, first housing tube portion 320 may comprise one or more apertures configured to produce a first stiffness of first housing tube portion 320. Illustratively, second housing tube portion 330 may comprise a solid portion of housing tube 300 having a second stiffness. In one or more embodiments, the second stiffness may be greater than the first stiffness. Illustratively, first housing tube portion 320 may comprise one or more apertures configured to produce a first stiffness of first housing tube portion 320. In one or more embodiments, second housing tube portion 330 may comprise one or more apertures configured to produce a second stiffness of second houses ing tube portion 330. Illustratively, the second stiffness may be greater than the first stiffness.

In one or more embodiments, first housing tube portion 320 may comprise a plurality of slits configured to separate one or more solid portions of housing tube 300. Illustratively, a plurality of slits may be cut, e.g., laser cut, into first housing tube portion 320. In one or more embodiments, first housing tube portion 320 may comprise a plurality of slits configured to minimize a force of friction between housing tube 300 and a cannula, e.g., as housing tube 300 is inserted into the cannula or as housing tube 300 is extracted from the cannula. For example, each slit of the plurality of slits may comprise one or more arches configured to minimize a force of friction between housing tube 300 and a cannula.

FIG. 3C illustrates an angled view of housing tube 300. Illustratively, an optic fiber 350 may be disposed within housing tube 300. In one or more embodiments, optic fiber 350 may be disposed within housing tube 300 wherein an optic fiber distal end 351 may be adjacent to housing tube distal end 301. Illustratively, optic fiber 350 may be disposed within housing tube 300 wherein a portion of optic fiber 350 may be adjacent to a portion of first housing tube portion 320. In one or more embodiments, a portion of optic fiber 350 may be fixed to an inner portion of housing tube 300, e.g., by a biocompatible adhesive or any other suitable means.

Figure 4:
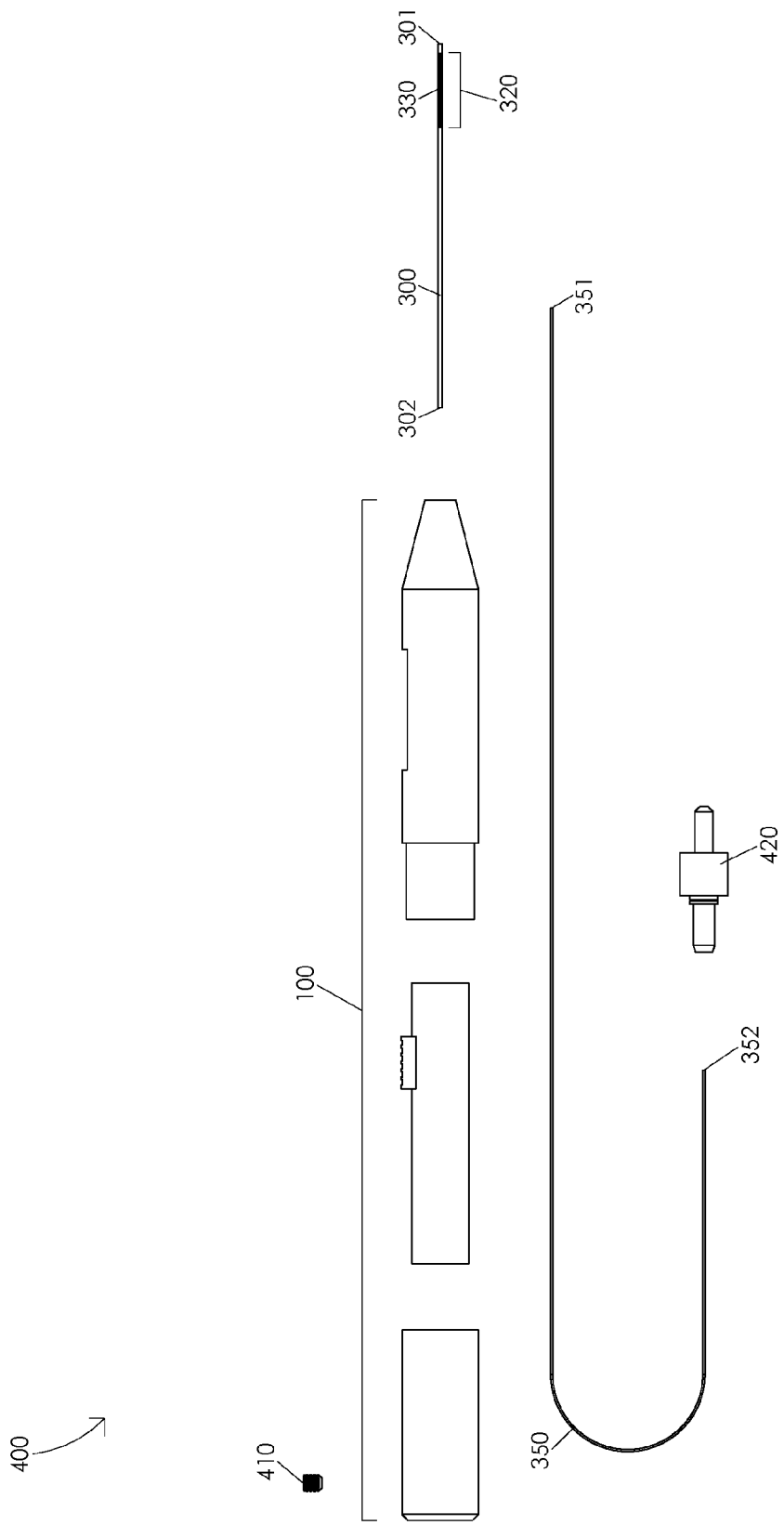
FIG. 4 is a schematic diagram illustrating an exploded view of a steerable laser probe assembly.

FIG. 4 is a schematic diagram illustrating an exploded view of a steerable laser probe assembly 400. In one or more embodiments, a steerable laser probe assembly 400 may comprise a handle assembly 100, a housing tube 300 having a housing tube distal end 301 and a housing tube proximal end 302, an optic fiber 350 having an optic fiber distal end 351 and an optic fiber proximal end 352, a fixation mechanism 410, and a light source interface 420. Illustratively, light source interface 420 may be configured to interface with optic fiber proximal end 352. In one or more embodiments, light source interface 420 may comprise a standard light source connector, e.g., an SMA connector.

Illustratively, housing tube 300 may be disposed within housing tube housing 180 and housing tube guide 185. In one or more embodiments, housing tube 300 may be fixed within housing tube housing 180, e.g., housing tube proximal end 302 may be fixed within housing tube housing 180. Illustratively, housing tube 300 may be fixed within housing tube housing 180, e.g., by an adhesive or by any suitable fixation means. In one or more embodiments, an actuation of actuation mechanism 120 may be configured to actuate housing tube 300. Illustratively, actuation control 130 may be configured to control an actuation of housing tube 300. In one or more embodiments, an actuation of actuation control 130 within actuation channel 135 may be configured to actuate housing tube 300 relative to handle base 140. Illustratively, an actuation of actuation control distal end 131 towards actuation channel distal end 136 may be configured to extend housing tube 300 relative to handle proximal end 202. In one or more embodiments, an actuation of actuation control proximal end 132 towards actuation channel proximal end 137 may be configured to retract housing tube 300 relative to handle proximal end 202.

Illustratively, optic fiber 350 may be disposed within inner bore 160, fixation mechanism housing 150, actuation mechanism guide 170, housing tube housing 180, housing tube guide 185, and housing tube 300. In one or more embodiments, fixation mechanism 410 may be disposed within fixation mechanism housing 150. Illustratively, fixation mechanism 410 may be configured to fix optic fiber 350 in a position relative to handle 200, e.g., at fixation mechanism housing 150. In one or more embodiments, fixation mechanism 410 may comprise a set screw configured to fix optic fiber 350 in a position relative to handle 200. Illustratively, optic fiber 350 may be fixed to fixation mechanism 410, e.g., by an adhesive or any suitable fixation means. For example, fixation mechanism 410 may be configured to fix optic fiber 350 in a position relative to handle 200, e.g., by an interference fit configured to fix optic fiber 350 in a position relative to handle 200 without damaging optic fiber 350. In one or more embodiments, a portion of optic fiber 350 may be fixed to an inner portion of housing tube 300, e.g., by an adhesive or any suitable fixation means. Illustratively, optic fiber 350 may be fixed in a position relative to handle 200, e.g., by fixation mechanism 410, and optic fiber 350 may also be fixed to an inner portion of housing tube 300, e.g., a first housing tube portion 320.

In one or more embodiments, an actuation of actuation mechanism 120 may be configured to actuate housing tube 300 relative to optic fiber 350. Illustratively, actuation control 130 may be configured to control an actuation of actuation mechanism 120 and housing tube 300. In one or more embodiments, an actuation of actuation control distal end 131 towards actuation channel distal end 136 may be configured to actuate actuation mechanism distal end 121 towards handle distal end 201. Illustratively, an actuation of actuation mechanism distal end 121 towards handle distal end 201 may be configured to extend housing tube 300 relative to optic fiber 350 and handle proximal end 202. In one or more embodiments, an actuation of actuation control proximal end 132 towards actuation channel proximal end 137 may be configured to actuate actuation mechanism proximal end 122 towards handle proximal end 202. Illustratively, an actuation of actuation mechanism proximal end 122 towards handle proximal end 202 may be configured to retract housing tube 300 relative to optic fiber 350 and handle proximal end 202.

In one or more embodiments, optic fiber 350 may be configured to resist an extension of housing tube 300 relative to handle proximal end 202. Illustratively, optic fiber 350 may be fixed in a position relative to handle 200, e.g., by fixation mechanism 410, and a portion of optic fiber 350 may be fixed to an inner portion of housing tube 300, e.g., a first housing tube portion 320. In one or more embodiments, as housing tube 300 is extended relative to handle proximal end 202, e.g., due to an actuation of actuation mechanism distal end 121 towards handle distal end 201, optic fiber 350 may be configured to resist the extension of housing tube 300 relative to handle proximal end 202. Illustratively, as housing tube 300 is gradually extended relative to handle proximal end 202, optic fiber 350 may be configured to gradually compress a portion of housing tube 300, e.g., a first housing tube portion 320, causing housing tube 300 to gradually curve. In one or more embodiments, a gradual curving of housing tube 300 may be configured to gradually curve optic fiber 350.

Illustratively, a retraction of housing tube 300 relative to handle proximal end 202, e.g., due to an actuation of actuation mechanism proximal end 122 towards handle proximal end 202, may be configured to reduce a compressive force applied, e.g., by optic fiber 350, to a portion of housing tube 300. In one or more embodiments, a gradual retraction of housing tube 300 relative to handle proximal end 202 may be configured to gradually decompress a portion of housing tube 300, e.g., a first housing tube portion 320, causing housing tube 300 to gradually straighten. Illustratively, a gradual straightening of housing tube 300 may be configured to gradually straighten optic fiber 350.

In one or more embodiments, an extension of actuation control 130 relative to handle proximal end 202 may comprise an actuation of actuation control distal end 131 towards actuation channel distal end 136. Illustratively, actuation control 130 may be fully extended relative to handle proximal end 202, e.g., when actuation control distal end 131 is adjacent to actuation channel distal end 136. In one or more embodiments, an extension of actuation mechanism 120 relative to handle proximal end 202 may comprise an actuation of actuation mechanism distal end 121 towards handle distal end 201. Illustratively, an extension of actuation control 130 relative to handle proximal end 202 may be configured to cause an extension of actuation mechanism 120 relative to handle proximal end 202. In one or more embodiments, an extension of actuation mechanism 120 relative to handle proximal end 202 may be configured to extend housing tube 300 relative to handle proximal end 202 and optic fiber 350. Illustratively, an extension of housing tube 300 relative to optic fiber 350 may be configured to curve housing tube 300. In one or more embodiments, a curving of housing tube 300 may be configured to curve optic fiber 350.

In one or more embodiments, a retraction of actuation control 130 relative to handle proximal end 202 may comprise an actuation of actuation control proximal end 132 towards actuation channel proximal end 137. Illustratively, actuation control 130 may be fully retracted relative to handle proximal end 202, e.g., when actuation control proximal end 132 is adjacent to actuation channel proximal end 137. In one or more embodiments, a retraction of actuation mechanism 120 relative to handle proximal end 202 may comprise an actuation of actuation mechanism proximal end 122 towards handle proximal end 202. Illustratively, a retraction of actuation control 130 relative to handle proximal end 202 may be configured to cause a retraction of actuation mechanism 120 relative to handle proximal end 202. In one or more embodiments, a retraction of actuation mechanism 120 relative to handle proximal end 202 may be configured to retract housing tube 300 relative to handle proximal end 202 and optic fiber 350. Illustratively, a retraction of housing tube 300 relative to optic fiber 350 may be configured to straighten housing tube 300. In one or more embodiments, a straightening of housing tube 300 may be configured to straighten optic fiber 350.

Figure 5A:
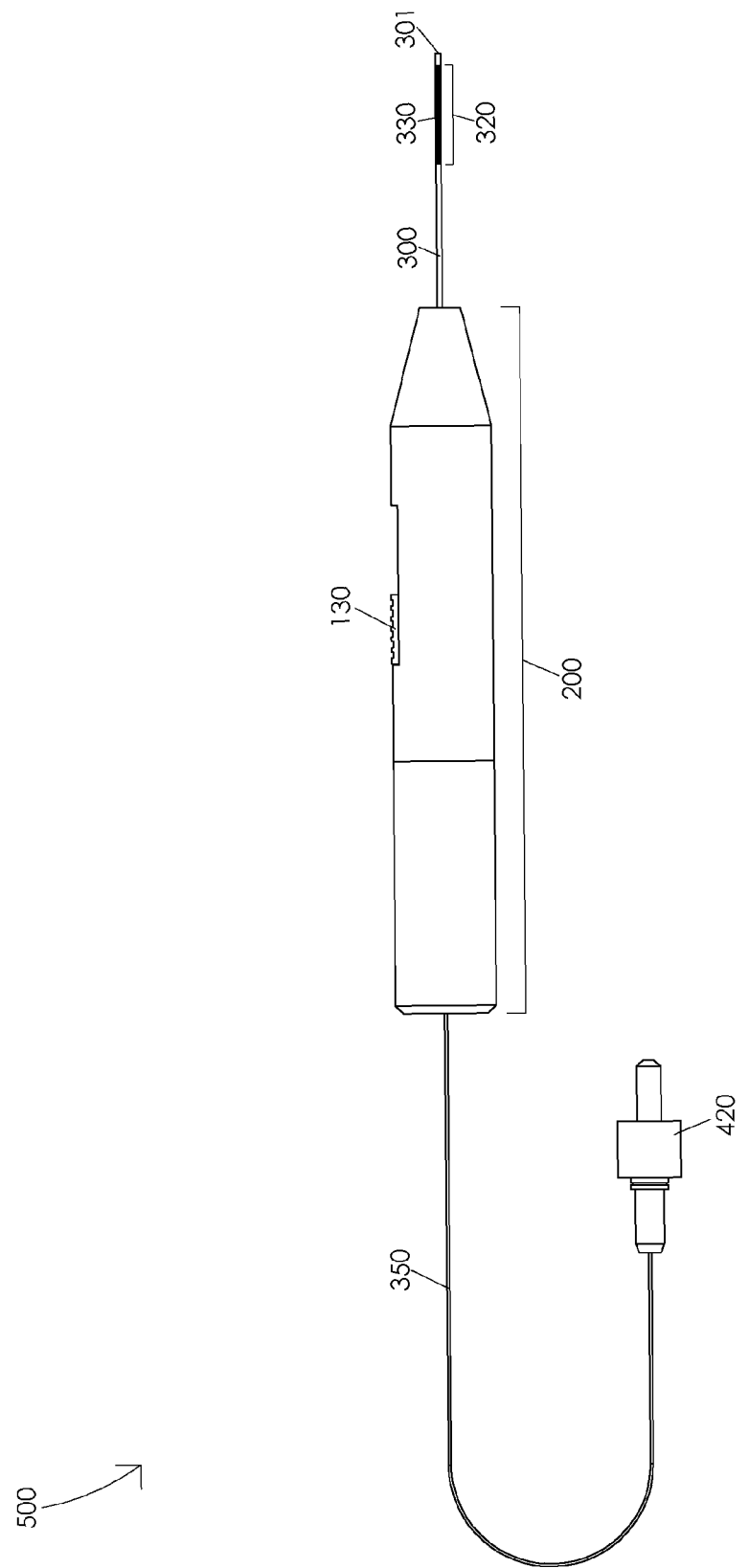
FIGS. 5A, 5B, 5C, 5D, and 5E illustrate a gradual curving of an optic fiber.

FIGS. 5A, 5B, 5C, 5D, and 5E illustrate a gradual curving of an optic fiber 350. FIG. 5A illustrates a straight optic fiber 500. In one or more embodiments, optic fiber 350 may comprise a straight optic fiber 500, e.g., when actuation control 130 is fully retracted relative to handle proximal end 202. Illustratively, optic fiber 350 may comprise a straight optic fiber 500, e.g., when first housing tube portion 320 is fully decompressed. In one or more embodiments, a line tangent to optic fiber distal end 351 may be parallel to a line tangent to housing tube proximal end 302, e.g., when optic fiber 350 comprises a straight optic fiber 500.

Figure 5B:
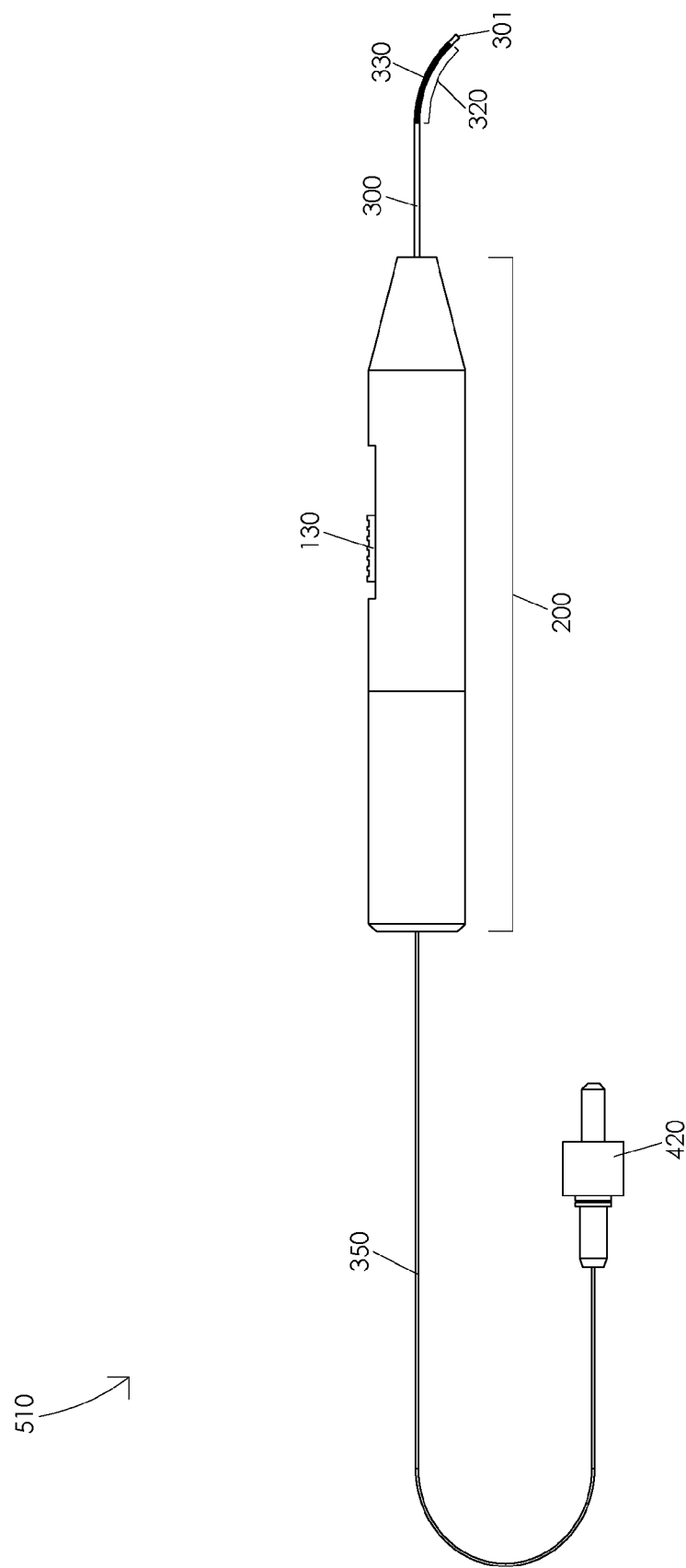

FIG. 5B illustrates an optic fiber in a first curved position 510. Illustratively, an extension of actuation control 130 relative to handle proximal end 202 may be configured to extend housing tube 300 relative to optic fiber 350. In one or more embodiments, an extension of housing tube 300 relative to optic fiber 350 may be configured to cause optic fiber 350 to compress a portion of housing tube 300 causing housing tube 300 to gradually curve. Illustratively, a gradual curving of housing tube 300 may be configured to gradually curve optic fiber 350. In one or more embodiments, an extension of actuation control 130 relative to handle proximal end 202 may be configured to gradually curve optic fiber 350 from a straight optic fiber 500 to an optic fiber in a first curved position 510. Illustratively, an extension of actuation mechanism 120 relative to handle proximal end 202 may be configured to extend housing tube 300 relative to optic fiber 350. In one or more embodiments, an extension of housing tube 300 relative to optic fiber 350 may be configured to gradually curve optic fiber 350 from a straight optic fiber 500 to an optic fiber in a first curved position 510. Illustratively, a line tangent to optic fiber distal end 351 may intersect a line tangent to housing tube proximal end 302 at a first angle, e.g., when optic fiber 350 comprises an optic fiber in a first curved position 510. In one or more embodiments, the first angle may comprise any angle greater than zero degrees. For example, the first angle may comprise a 45 degree angle.

Figure 5C:
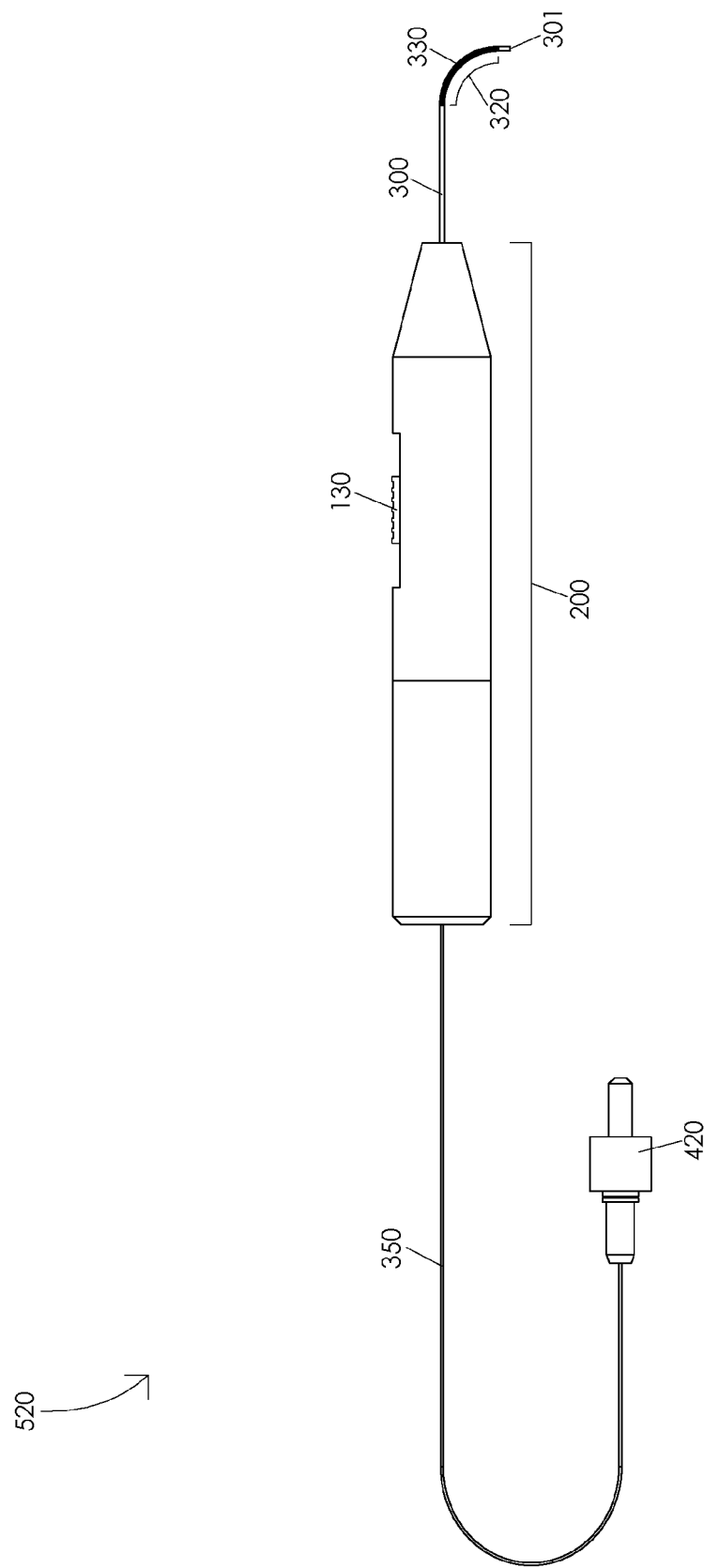

FIG. 5C illustrates an optic fiber in a second curved position 520. Illustratively, an extension of actuation control 130 relative to handle proximal end 202 may be configured to extend housing tube 300 relative to optic fiber 350. In one or more embodiments, an extension of housing tube 300 relative to optic fiber 350 may be configured to cause optic fiber 350 to compress a portion of housing tube 300 causing housing tube 300 to gradually curve. Illustratively, a gradual curving of housing tube 300 may be configured to gradually curve optic fiber 350. In one or more embodiments, an extension of actuation control 130 relative to handle proximal end 202 may be configured to gradually curve optic fiber 350 from an optic fiber in a first curved position 510 to an optic fiber in a second curved position 520. Illustratively, an extension of actuation mechanism 120 relative to handle proximal end 202 may be configured to extend housing tube 300 relative to optic fiber 350. In one or more embodiments, an extension of housing tube 300 relative to optic fiber 350 may be configured to gradually curve optic fiber 350 from an optic fiber in a first curved position 510 to an optic fiber in a second curved position 520. Illustratively, a line tangent to optic fiber distal end 351 may intersect a line tangent to housing tube proximal end 302 at a second angle, e.g., when optic fiber 350 comprises an optic fiber in a second curved position 520. In one or more embodiments, the second angle may comprise any angle greater than the first angle. For example, the second angle may comprise a 90 degree angle.

Figure 5D:
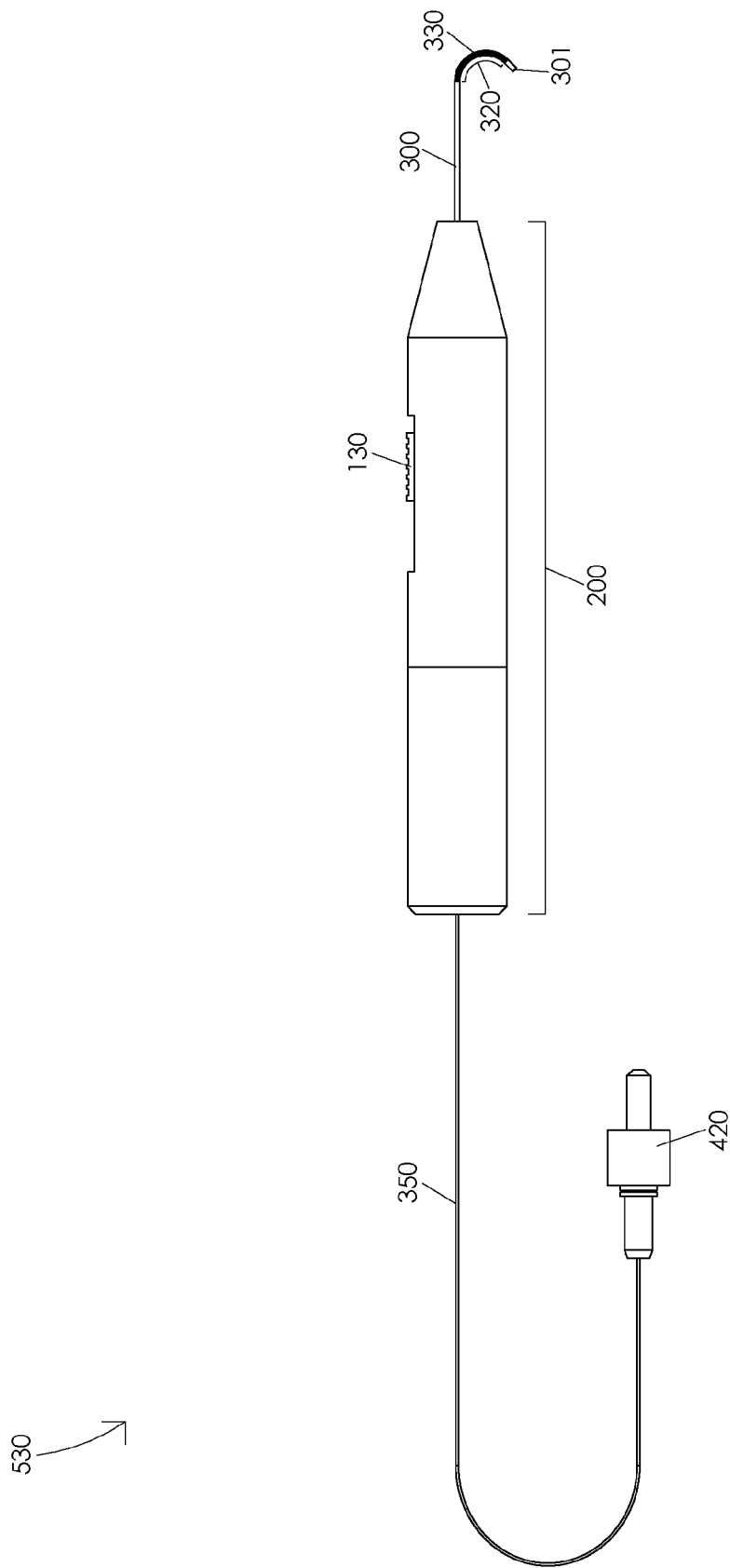

FIG. 5D illustrates an optic fiber in a third curved position 530. Illustratively, an extension of actuation control 130 relative to handle proximal end 202 may be configured to extend housing tube 300 relative to optic fiber 350. In one or more embodiments, an extension of housing tube 300 relative to optic fiber 350 may be configured to cause optic fiber 350 to compress a portion of housing tube 300 causing housing tube 300 to gradually curve. Illustratively, a gradual curving of housing tube 300 may be configured to gradually curve optic fiber 350. In one or more embodiments, an extension of actuation control 130 relative to handle proximal end 202 may be configured to gradually curve optic fiber 350 from an optic fiber in a second curved position 520 to an optic fiber in a third curved position 530. Illustratively, an extension of actuation mechanism 120 relative to handle proximal end 202 may be configured to extend housing tube 300 relative to optic fiber 350. In one or more embodiments, an extension of housing tube 300 relative to optic fiber 350 may be configured to gradually curve optic fiber 350 from an optic fiber in a second curved position 520 to an optic fiber in a third curved position 530. Illustratively, a line tangent to optic fiber distal end 351 may intersect a line tangent to housing tube proximal end 302 at a second angle, e.g., when optic fiber 350 comprises an optic fiber in a third curved position 530. In one or more embodiments, the third angle may comprise any angle greater than the second angle. For example, the third angle may comprise a 135 degree angle.

Figure 5E:
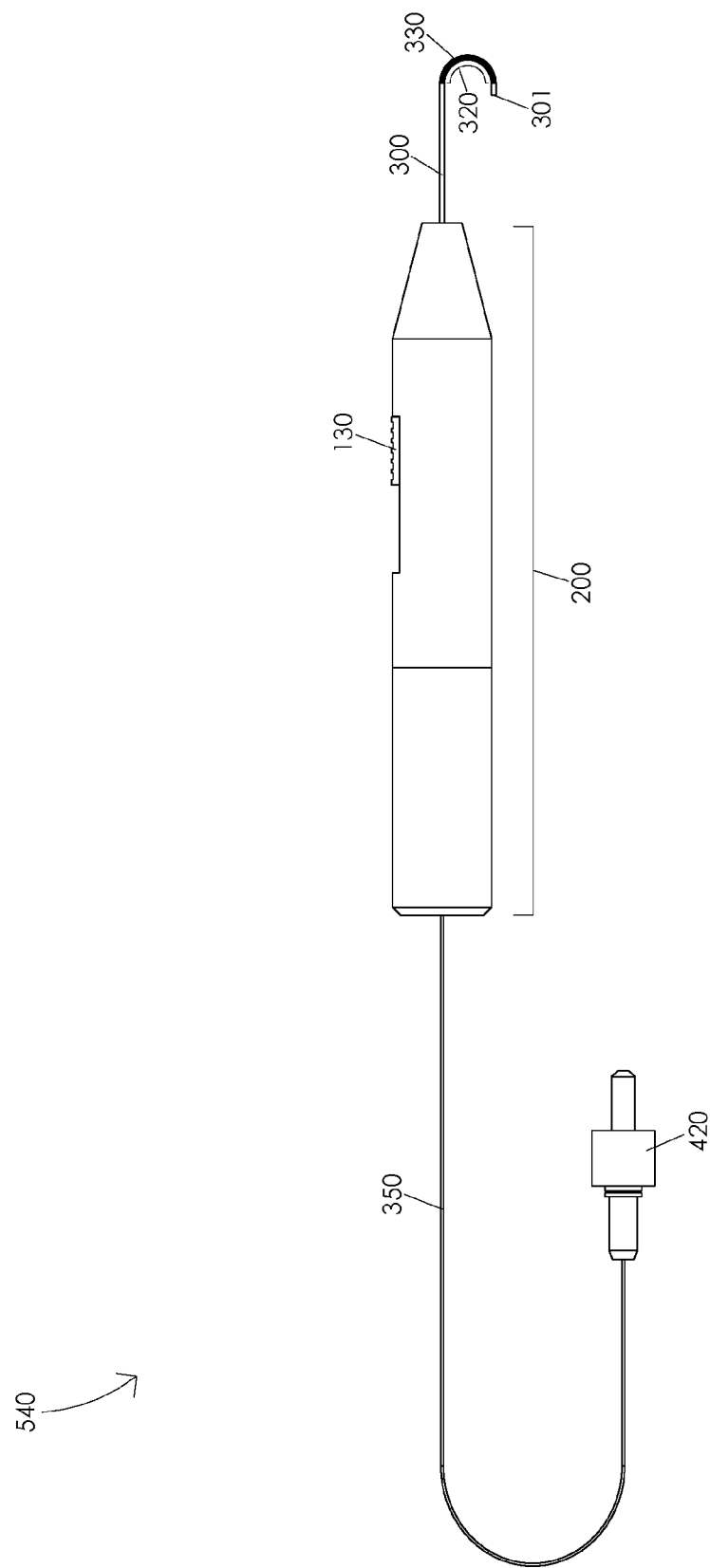

FIG. 5E illustrates an optic fiber in a fourth curved position 540. Illustratively, an extension of actuation control 130 relative to handle proximal end 202 may be configured to extend housing tube 300 relative to optic fiber 350. In one or more embodiments, an extension of housing tube 300 relative to optic fiber 350 may be configured to cause optic fiber 350 to compress a portion of housing tube 300 causing housing tube 300 to gradually curve. Illustratively, a gradual curving of housing tube 300 may be configured to gradually curve optic fiber 350. In one or more embodiments, an extension of actuation control 130 relative to handle proximal end 202 may be configured to gradually curve optic fiber 350 from an optic fiber in a third curved position 530 to an optic fiber in a fourth curved position 540. Illustratively, an extension of actuation mechanism 120 relative to handle proximal end 202 may be configured to extend housing tube 300 relative to optic fiber 350. In one or more embodiments, an extension of housing tube 300 relative to optic fiber 350 may be configured to gradually curve optic fiber 350 from an optic fiber in a third curved position 530 to an optic fiber in a fourth curved position 540. For example, a line tangent to optic fiber distal end 351 may be parallel to a line tangent to housing tube proximal end 302, e.g., when optic fiber 350 comprises an optic fiber in a fourth curved position 540.

In one or more embodiments, one or more properties of a steerable laser probe may be adjusted to attain one or more desired steerable laser probe features. For example, a stiffness of first housing tube portion 320 or a stiffness of second housing tube portion 330 may be adjusted to vary an amount of actuation of actuation mechanism 120 configured to curve housing tube 300 to a particular curved position. Illustratively, a material comprising first housing tube portion 320 or a material comprising second housing tube portion 330 may be adjusted to vary an amount of actuation of actuation mechanism 120 configured to curve housing tube 300 to a particular curved position. In one or more embodiments, an inner diameter of first housing tube portion 320 or an inner diameter of second housing tube portion 330 may be adjusted to vary an amount of actuation structure 120 configured to curve housing tube 300 to a particular curved position. Illustratively, an outer diameter of first housing tube portion 320 or an outer diameter of second housing tube portion 330 may be adjusted to vary an amount of actuation structure 120 configured to curve housing tube 300 to a particular curved position.

In one or more embodiments, a number of apertures in housing tube 300 may be adjusted to vary an amount of actuation of actuation mechanism 120 configured to curve housing tube 300 to a particular curved position. Illustratively, a location of one or more apertures in housing tube 300 may be adjusted to vary an amount of actuation of actuation mechanism 120 configured to curve housing tube 300 to a particular curved position. In one or more embodiments, a geometry of one or more apertures in housing tube 300 may be adjusted to vary an amount of actuation of actuation mechanism 120 configured to curve housing tube 300 to a particular curved position. Illustratively, a geometry of one or more apertures in housing tube 300 may be uniform, e.g., each aperture of the one or more apertures may have a same geometry. In one or more embodiments, a geometry of one or more apertures in housing tube 300 may be non-uniform, e.g., a first aperture in housing tube 300 may have a first geometry and a second aperture in housing tube 300 may have a second geometry.

Illustratively, a geometry or shape of actuation mechanism 120 may be adjusted to vary an amount actuation of actuation mechanism 120 configured to curve housing tube 300 to a particular curved position. In one or more embodiments, one or more locations within housing tube 300 wherein optic fiber 350 may be fixed to an inner portion of housing tube 300 may be adjusted to vary an amount of actuation of actuation mechanism 120 configured to curve housing tube 300 to a particular curved position. Illustratively, at least a portion of optic fiber 350 may be enclosed in an optic fiber sleeve configured to, e.g., protect optic fiber 350, vary a stiffness of optic fiber 350, vary an optical property of optic fiber 350, etc. For example, a portion of optic fiber 350 that may be fixed to fixation mechanism 410, e.g., at fixation mechanism housing 150, may be enclosed in an optic fiber sleeve configured to, e.g., protect optic fiber 350, facilitate a fixation, etc. In one or more embodiments, a portion of optic fiber 350 that may be fixed to an inner portion of housing tube 300 may be enclosed in an optic fiber sleeve configured to, e.g., protect optic fiber 350, facilitate a fixation, etc. Illustratively, a portion of housing tube 300 may comprise an access window, e.g., configured to allow access to an inner portion of housing tube 300. In one or more embodiments, a portion of housing tube 300 may comprise an access window, e.g., configured to allow access to a portion of optic fiber 350.

Illustratively, a stiffness of first housing tube portion 320 or a stiffness of second housing tube portion 330 may be adjusted to vary a bend radius of housing tube 300. In one or more embodiments, a stiffness of first housing tube portion 320 or a stiffness of second housing tube portion 330 may be adjusted to vary a radius of curvature of housing tube 300, e.g., when housing tube 300 is in a particular curved position. Illustratively, a number of apertures in housing tube 300 may be adjusted to vary a bend radius of housing tube 300. In one or more embodiments, a number of apertures in housing tube 300 may be adjusted to vary a radius of curvature of housing tube 300, e.g., when housing tube 300 is in a particular curved position. Illustratively, a location or a geometry of one or more apertures in housing tube 300 may be adjusted to vary a bend radius of housing tube 300. In one or more embodiments, a location or a geometry of one or more apertures in housing tube 300 may be adjusted to vary a radius of curvature of housing tube 300, e.g., when housing tube 300 is in a particular curved position.

Figure 6A:
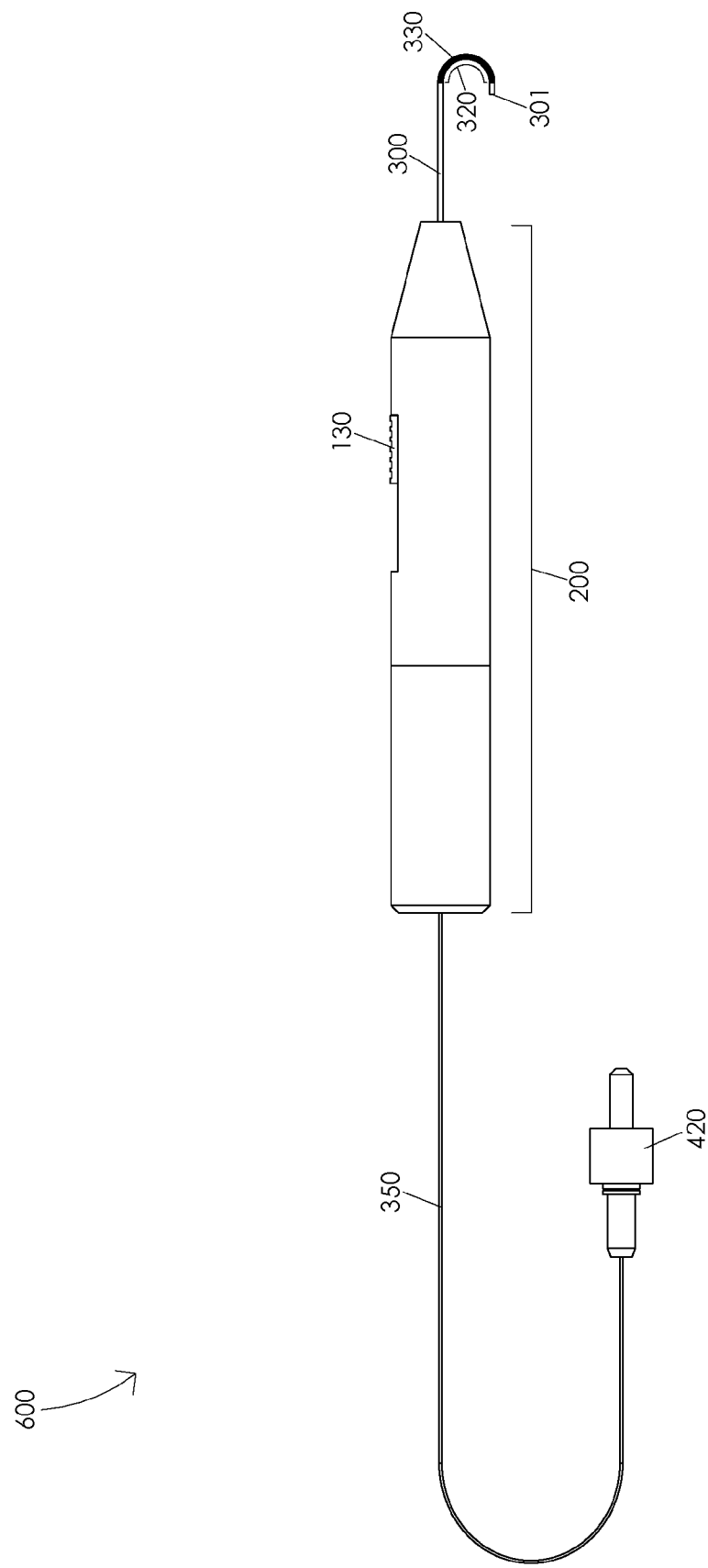
FIGS. 6A, 6B, 6C, 6D, and 6E illustrate a gradual straightening of an optic fiber.

FIGS. 6A, 6B, 6C, 6D, and 6E illustrate a gradual straightening of an optic fiber 350. FIG. 6A illustrates a fully curved optic fiber 600. In one or more embodiments, optic fiber 350 may comprise a fully curved optic fiber 600, e.g., when actuation control 130 is fully extended relative to handle proximal end 202. Illustratively, optic fiber 350 may comprise a fully curved optic fiber 600, e.g., when first housing tube portion 320 is fully compressed. In one or more embodiments, a line tangent to optic fiber distal end 351 may be parallel to a line tangent to housing tube proximal end 302, e.g., when optic fiber 350 comprises a straight optic fiber 600.

Figure 6B:
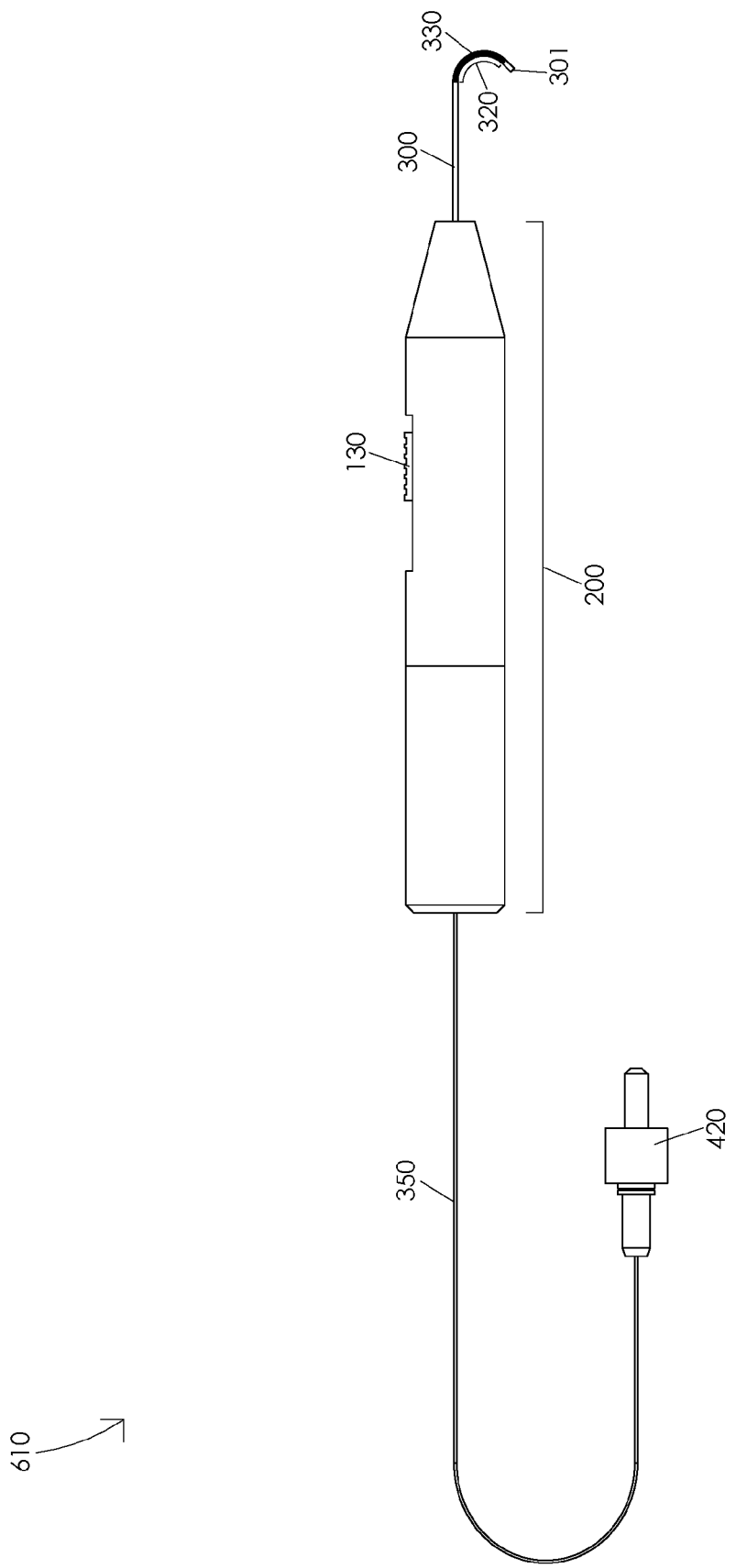

FIG. 6B illustrates an optic fiber in a first partially straightened position 610. Illustratively, a retraction of actuation control 130 relative to handle proximal end 202 may be configured to retract housing tube 300 relative to optic fiber 350. In one or more embodiments, a retraction of housing tube 300 relative to optic fiber 350 may be configured to cause optic fiber 350 to decompress a portion of housing tube 300, e.g., a first housing tube portion 320, causing housing tube 300 to gradually straighten. Illustratively, a gradual straightening of housing tube 300 may be configured to gradually straighten optic fiber 350. In one or more embodiments, a retraction of actuation control 130 relative to handle proximal end 202 may be configured to gradually straighten optic fiber 350 from a fully curved optic fiber 600 to an optic fiber in a first partially straightened position 610. Illustratively, a retraction of actuation mechanism 120 relative to handle proximal end 202 may be configured to retract housing tube 300 relative to optic fiber 350. In one or more embodiments, a retraction of housing tube 300 relative to optic fiber 350 may be configured to gradually straighten optic fiber 350 from a fully curved optic fiber 600 to an optic fiber in a first partially straightened position 610. Illustratively, a line tangent to optic fiber distal end 351 may intersect a line tangent to housing tube proximal end 302 at a first partially straightened angle, e.g., when optic fiber 350 comprises an optic fiber in a first partially straightened position 610. Illustratively, the first partially straightened angle may comprise any angle less than 180 degrees. For example, the first partially straightened angle may comprise a 135 degree angle.

Figure 6C:
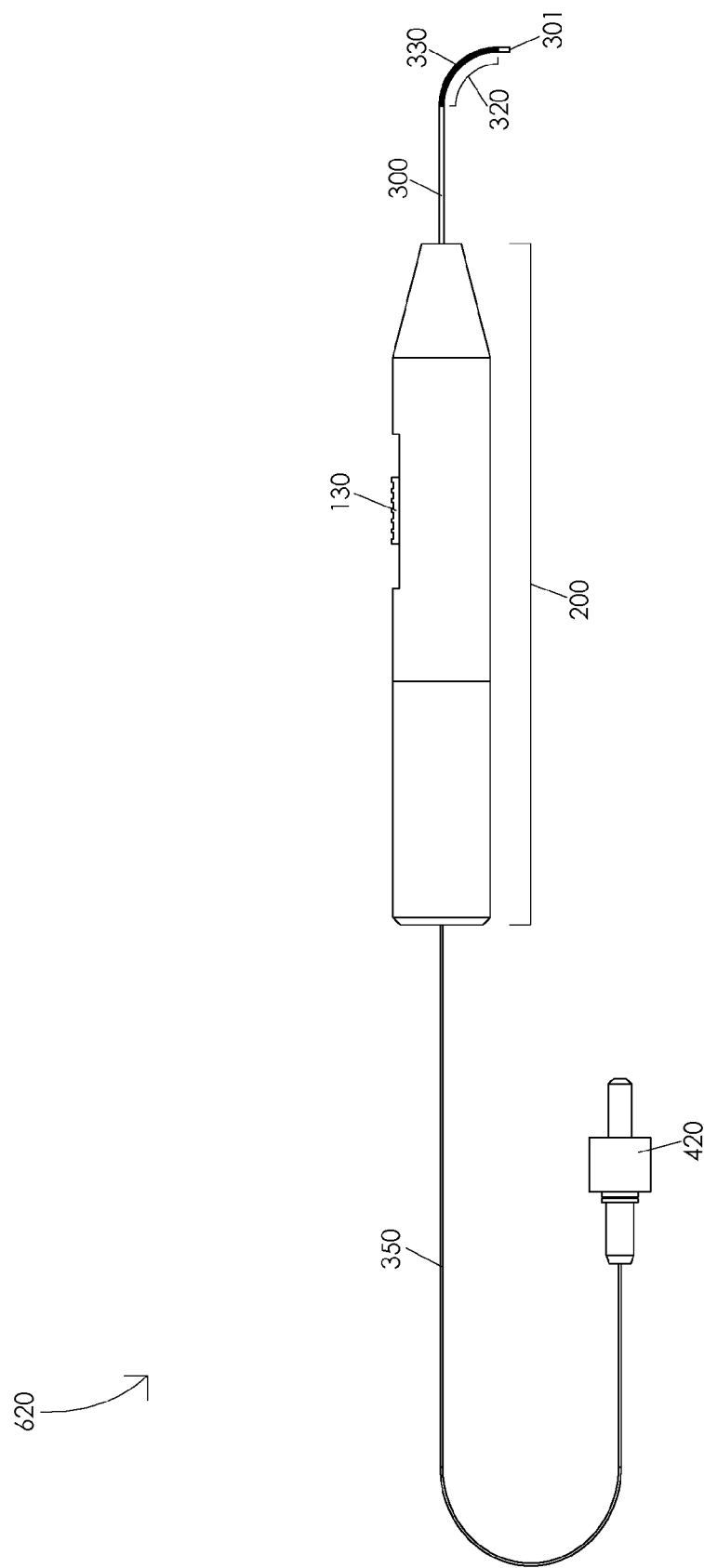

FIG. 6C illustrates an optic fiber in a second partially straightened position 620. Illustratively, a retraction of actuation control 130 relative to handle proximal end 202 may be configured to retract housing tube 300 relative to optic fiber 350. In one or more embodiments, a retraction of housing tube 300 relative to optic fiber 350 may be configured to cause optic fiber 350 to decompress a portion of housing tube 300, e.g., a first housing tube portion 320, causing housing tube 300 to gradually straighten. Illustratively, a gradual straightening of housing tube 300 may be configured to gradually straighten optic fiber 350. In one or more embodiments, a retraction of actuation control 130 relative to handle proximal end 202 may be configured to gradually straighten optic fiber 350 from an optic fiber in a first partially straightened position 610 to an optic fiber in a second partially straightened position 620. Illustratively, a retraction of actuation mechanism 120 relative to handle proximal end 202 may be configured to retract housing tube 300 relative to optic fiber 350. In one or more embodiments, a retraction of housing tube 300 relative to optic fiber 350 may be configured to gradually straighten optic fiber 350 from an optic fiber in a first partially straightened position 610 to an optic fiber in a second partially straightened position 620. Illustratively, a line tangent to optic fiber distal end 351 may intersect a line tangent to housing tube proximal end 302 at a second partially straightened angle, e.g., when optic fiber 350 comprises an optic fiber in a second partially straightened position 620. Illustratively, the second partially straightened angle may comprise any angle less than the first partially straightened angle. For example, the second partially straightened angle may comprise a 90 degree angle.

Figure 6D:
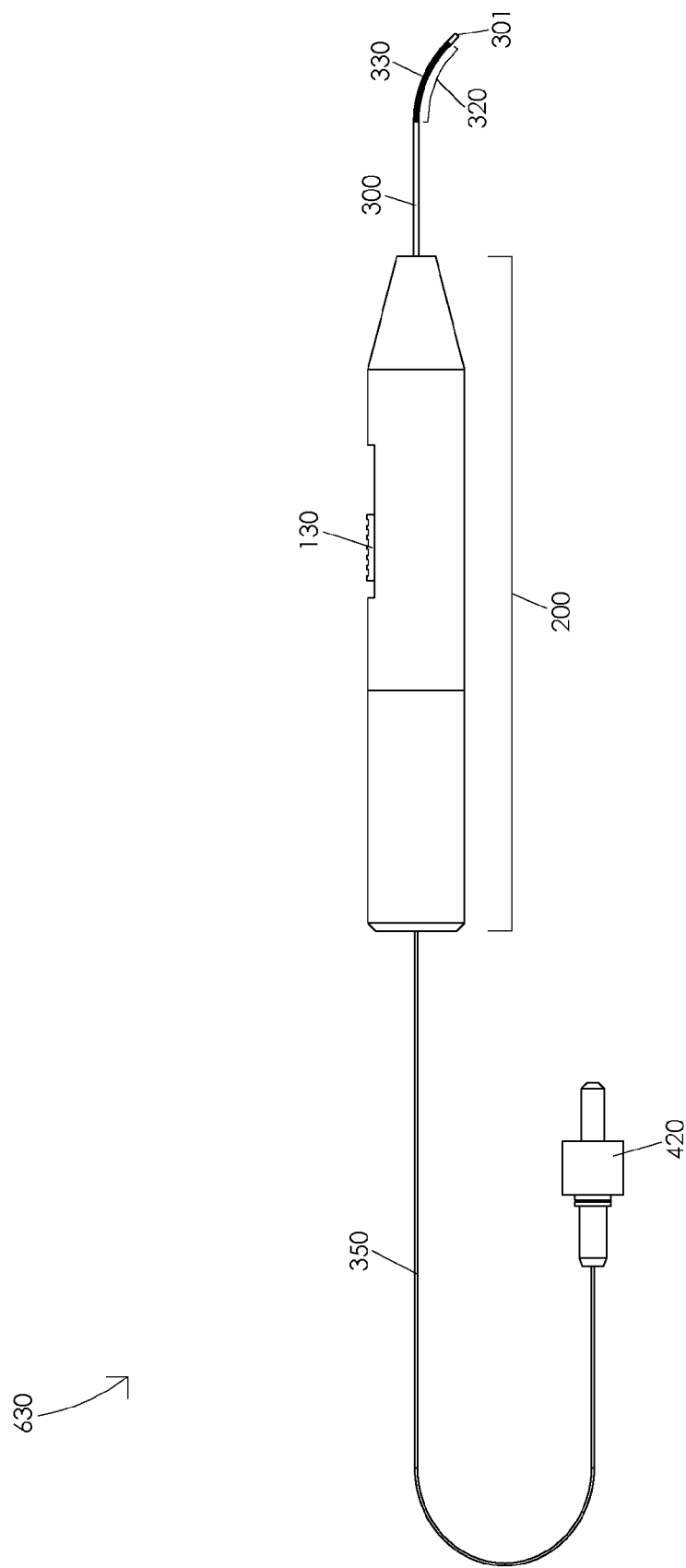

FIG. 6D illustrates an optic fiber in a third partially straightened position 630. Illustratively, a retraction of actuation control 130 relative to handle proximal end 202 may be configured to retract housing tube 300 relative to optic fiber 350. In one or more embodiments, a retraction of housing tube 300 relative to optic fiber 350 may be configured to cause optic fiber 350 to decompress a portion of housing tube 300, e.g., a first housing tube portion 320, causing housing tube 300 to gradually straighten. Illustratively, a gradual straightening of housing tube 300 may be configured to gradually straighten optic fiber 350. In one or more embodiments, a retraction of actuation control 130 relative to handle proximal end 202 may be configured to gradually straighten optic fiber 350 from an optic fiber in a second partially straightened position 620 to an optic fiber in a third partially straightened position 630. Illustratively, a retraction of actuation mechanism 120 relative to handle proximal end 202 may be configured to retract housing tube 300 relative to optic fiber 350. In one or more embodiments, a retraction of housing tube 300 relative to optic fiber 350 may be configured to gradually straighten optic fiber 350 from an optic fiber in a second partially straightened position 620 to an optic fiber in a third partially straightened position 630. Illustratively, a line tangent to optic fiber distal end 351 may intersect a line tangent to housing tube proximal end 302 at a third partially straightened angle, e.g., when optic fiber 350 comprises an optic fiber in a third partially straightened position 630. Illustratively, the third partially straightened angle may comprise any angle less than the second partially straightened angle. For example, the third partially straightened angle may comprise a 45 degree angle.

Figure 6E:
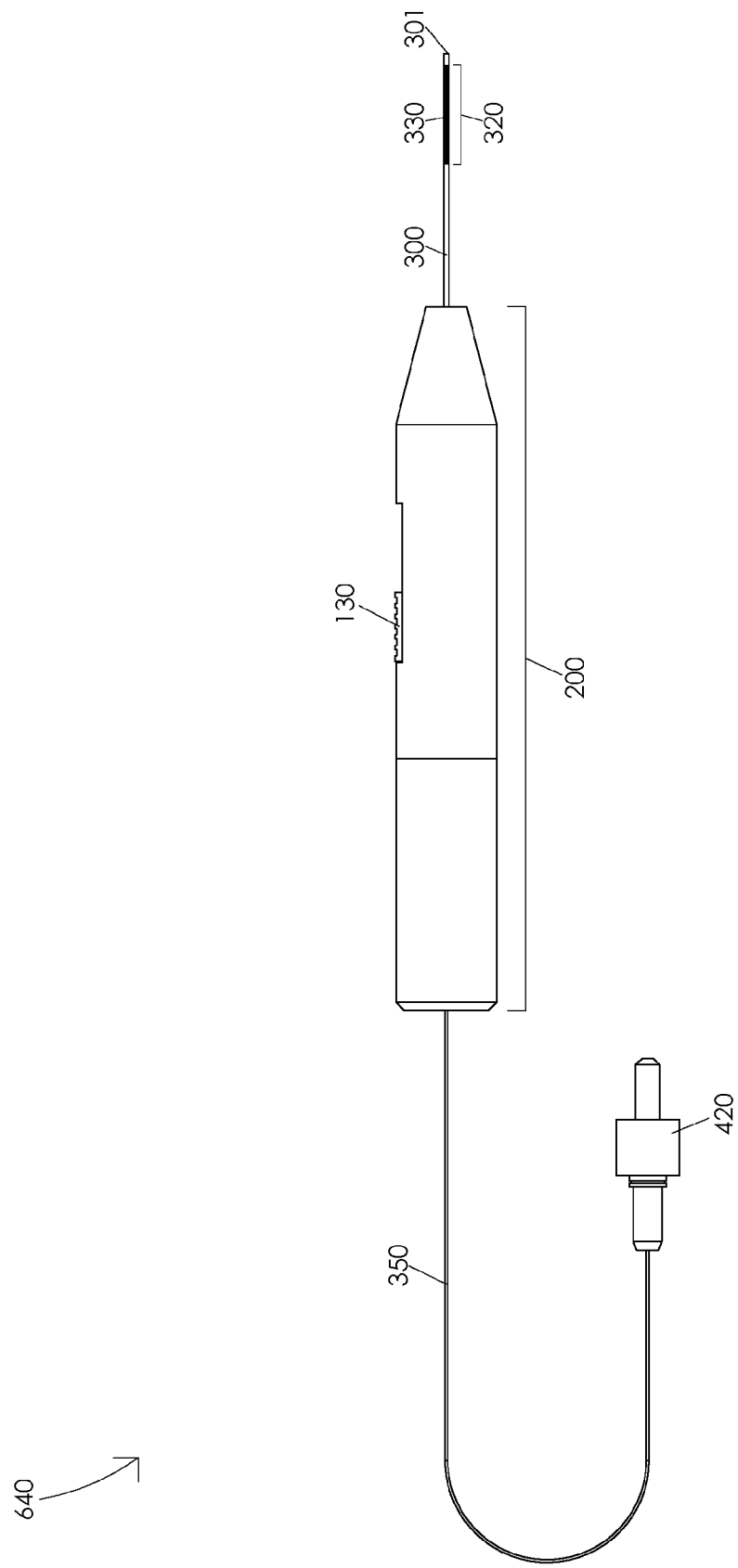

FIG. 6E illustrates an optic fiber in a fully straightened position 640. Illustratively, a retraction of actuation control 130 relative to handle proximal end 202 may be configured to retract housing tube 300 relative to optic fiber 350. In one or more embodiments, a retraction of housing tube 300 relative to optic fiber 350 may be configured to cause optic fiber 350 to decompress a portion of housing tube 300, e.g., a first housing tube portion 320, causing housing tube 300 to gradually straighten. Illustratively, a gradual straightening of housing tube 300 may be configured to gradually straighten optic fiber 350. In one or more embodiments, a retraction of actuation control 130 relative to handle proximal end 202 may be configured to gradually straighten optic fiber 350 from an optic fiber in a third partially straightened position 630 to an optic fiber in a fully straightened position 640. Illustratively, a retraction of actuation mechanism 120 relative to handle proximal end 202 may be configured to retract housing tube 300 relative to optic fiber 350. In one or more embodiments, a retraction of housing tube 300 relative to optic fiber 350 may be configured to gradually straighten optic fiber 350 from an optic fiber in a third partially straightened position 630 to an optic fiber in a fully straightened position 640. Illustratively, a line tangent to optic fiber distal end 351 may be parallel to a line tangent to housing tube proximal end 302, e.g., when optic fiber 350 comprises an optic fiber in a fully straightened position 640.

Illustratively, a surgeon may aim optic fiber distal end 351 at any of a plurality of targets within an eye, e.g., to perform a photocoagulation procedure. In one or more embodiments, a surgeon may aim optic fiber distal end 351 at any target within a particular transverse plane of the inner eye by, e.g., rotating handle 200 to orient housing tube 300 in an orientation configured to cause a curvature of housing tube 300 within the particular transverse plane of the inner eye and varying an amount of actuation of actuation mechanism 120. Illustratively, a surgeon may aim optic fiber distal end 351 at any target within a particular sagittal plane of the inner eye by, e.g., rotating handle 200 to orient housing tube 300 in an orientation configured to cause a curvature of housing tube 300 within the particular sagittal plane of the inner eye and varying an amount of actuation of actuation mechanism 120. In one or more embodiments, a surgeon may aim optic fiber distal end 351 at any target within a particular frontal plane of the inner eye by, e.g., varying an amount of actuation of actuation mechanism 120 to orient a line tangent to optic fiber distal end 351 wherein the line tangent to optic fiber distal end 351 is within the particular frontal plane of the inner eye and rotating handle 200. Illustratively, a surgeon may aim optic fiber distal end 351 at any target located outside of the particular transverse plane, the particular sagittal plane, and the particular frontal plane of the inner eye, e.g., by varying a rotational orientation of handle 200 and varying an amount of actuation of actuation mechanism 120. In one or more embodiments, a surgeon may aim optic fiber distal end 351 at any target of a plurality of targets within an eye, e.g., without increasing a length of a portion of a steerable laser probe within the eye. Illustratively, a surgeon may aim optic fiber distal end 351 at any target of a plurality of targets within an eye, e.g., without decreasing a length of a portion of a steerable laser probe within the eye.

Figure 7A:
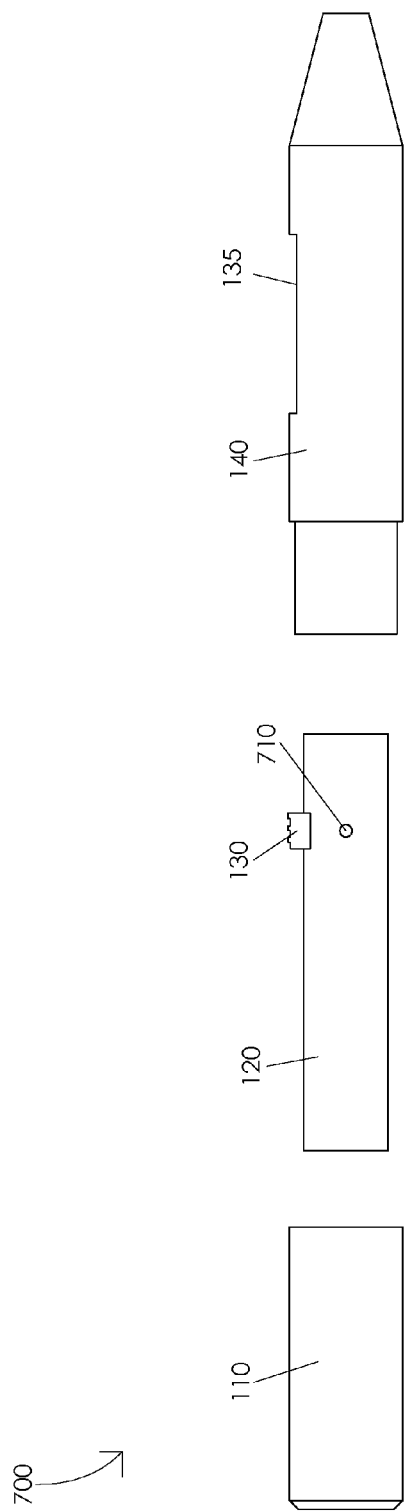
FIGS. 7A and 7B are schematic diagrams illustrating an exploded view of a handle assembly.
Figure 7B:
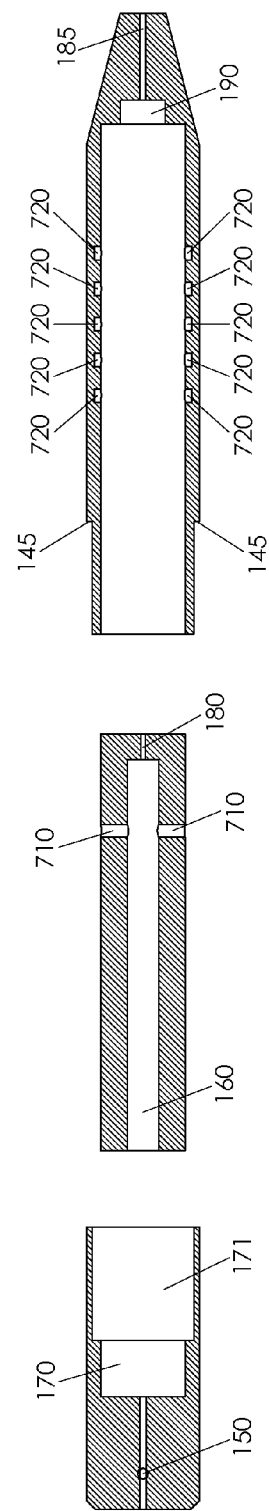

FIGS. 7A and 7B are schematic diagrams illustrating an exploded view of a handle assembly 700. FIG. 7A illustrates a side view of a handle assembly 700. In one or more embodiments, a handle assembly 700 may comprise an outer cylinder 110, an actuation mechanism 120, and a handle base 140. Illustratively, actuation mechanism 120 may comprise an actuation control 130. In one or more embodiments, handle base 140 may comprise an actuation channel 135. Illustratively, actuation mechanism 120 may comprise an actuation chamber 710. FIG. 7B illustrates a cross-sectional top view of a handle assembly 700. In one or more embodiments, handle base 140 may comprise one or more static chambers 720.

FIGS. 8A and 8B are schematic diagrams illustrating a handle 800. FIG. 8A illustrates a transparent top view of handle 800. In one or more embodiments, actuation control 130 may be disposed within actuation channel 135. FIG. 8B illustrates a transparent side view of handle 800. Illustratively, an actuation chamber 710 may be configured to align with one or more static chambers 720. In one or more embodiments, one or more static chambers 720 may be configured to temporarily fix actuation control 130 in a position within actuation channel 135. For example, a first static chamber 720 may be configured to temporarily fix actuation control 130 in a first position within actuation channel 135, a second static chamber 720 may be configured to temporarily fix actuation control 130 in a second position within actuation channel 135, a third static chamber 720 may be configured to temporarily fix actuation control 130 in a third position within actuation channel 135, a forth static chamber 720 may be configured to temporarily fix actuation control 130 in a forth position within actuation channel 135, etc.

Illustratively, a static chamber 720 may be configured to interface with actuation chamber 710, e.g., to temporarily fix actuation control 130 in a position within actuation channel 135. In one or more embodiments, an interface between a static chamber 720 and actuation chamber 710 may be configured to align a static chamber 720 and actuation chamber 710 wherein a fixation pin may be temporarily disposed within a static chamber 720 and within actuation chamber 710. Illustratively, a fixation pin may be temporarily disposed within a static chamber 720 and within actuation chamber 710, e.g., by pushing the fixation pin into a static chamber 720 and into actuation chamber 710. In one or more embodiments, actuation control 130 may be temporarily fixed in a position within actuation channel 135, e.g., when a fixation pin is disposed within a static chamber 720 and within actuation chamber 710. Illustratively, removing a fixation pin from actuation chamber 710 may be configured to allow actuation control 130 actuate within actuation channel 135. In one or more embodiments, a fixation pin may be removed from actuation chamber 710, e.g., by pulling the fixation pin out of actuation chamber 710.

Illustratively, one or more static chambers 720 may be configured to house one or more magnets 810. In one or more embodiments, actuation chamber 710 may be configured to house one or more magnets 810. Illustratively, one or more magnets 810 may be configured to temporarily fix actuation control 130 in a position within actuation channel 135. In one or more embodiments, one or more magnets 810 may be disposed within a static chamber 720 wherein one or more magnetic poles of the one or more magnets 810 may be oriented to cause an attractive force between one or more magnets 810 and actuation control 130, e.g., when actuation chamber 710 is adjacent to a static chamber 720. Illustratively, one or more magnets 810 may be disposed within actuation chamber 710 wherein one or more magnetic poles of the one or more magnets 810 may be oriented to cause an attractive force between one or more magnets 810 and a static chamber 720, e.g., when actuation chamber 710 is adjacent to a static chamber 720. In one or more embodiments, one or more magnets 810 may be configured to cause one or more attractive forces configured to temporarily fix actuation control 130 in a position within actuation channel 135. For example, an attractive force configured to temporarily fix actuation control 130 in a position within actuation channel 135 may have a magnitude in the range of 1 to 50 N. However, an attractive force con-figured to temporarily fix actuation control 130 in a position within actuation channel 135 may have a magnitude less than 1 N or a magnitude greater than 50 N. Illustratively, an application of a force, e.g., a force having a magnitude greater than a magnitude of an attractive force, to actuation control 130 may be configured to actuate actuation control 130 within actuation channel 135.

In one or more embodiments, temporarily fixing actuation control 130 in a position within actuation channel 135 may be configured to temporarily fix housing tube 300 in a particular curved position. Illustratively, temporarily fixing housing tube 300 in a particular curved position may be configured to temporarily fix optic fiber 350 in a particular curved position. In one or more embodiments, a first static chamber 720 may be configured to temporarily fix housing tube 300 in a particular curved position wherein optic fiber 350 may comprise an optic fiber in a first curved position 510, a second static chamber 720 may be configured to temporarily fix housing tube 300 in a particular curved position wherein optic fiber 350 may comprise an optic fiber in a second curved position 520, a third static chamber 720 may be configured to temporarily fix housing tube 300 in a particular curved position wherein optic fiber 350 may comprise an optic fiber in a third curved position 530, a fourth static chamber 720 may be configured to temporarily fix housing tube 300 in a particular curved position wherein optic fiber 350 may comprise an optic fiber in a fourth curved position 540, etc.

FIGS. 9A and 9B are schematic diagrams illustrating an exploded view of a handle assembly 900. FIG. 9A illustrates a side view of a handle assembly 900. In one or more embodiments, a handle assembly 900 may comprise an outer cylinder 910 having an outer cylinder distal end 911 and an outer cylinder proximal end 912, an actuation mechanism 920 having an actuation mechanism distal end 921 and an actuation mechanism proximal end 922, and a handle base 940 having a handle base distal end 941 and a handle base proximal end 942. Illustratively, actuation mechanism 920 may comprise an actuation control 930. In one or more embodiments, actuation control 930 may comprise an actuation control distal end 931 and an actuation control proximal end 932. Illustratively, handle base 940 may comprise an actuation channel 935 having an actuation channel distal end 936 and an actuation channel proximal end 937. In one or more embodiments, handle base 940 may comprise an outer cylinder interface 945. Illustratively, outer cylinder interface 945 may be configured to interface with outer cylinder 910, e.g., outer cylinder interface 945 may be configured to interface with outer cylinder distal end 911. FIG. 9B illustrates a cross-sectional view of a handle assembly 900. In one or more embodiments, a handle assembly 900 may comprise a fixation mechanism housing 950, an inner bore 960, an actuation mechanism guide 970, a handle base housing 971, a housing tube housing 980, a housing tube guide 985, and a pressure mechanism housing 990. Illustratively, handle base housing 971 may comprise a handle base interface 972. Outer cylinder 910, actuation mechanism 920, and handle base 940 may be manufactured from any suitable material, e.g., polymers, metals, metal alloys, etc., or from any combination of suitable materials.

Figure 10A:
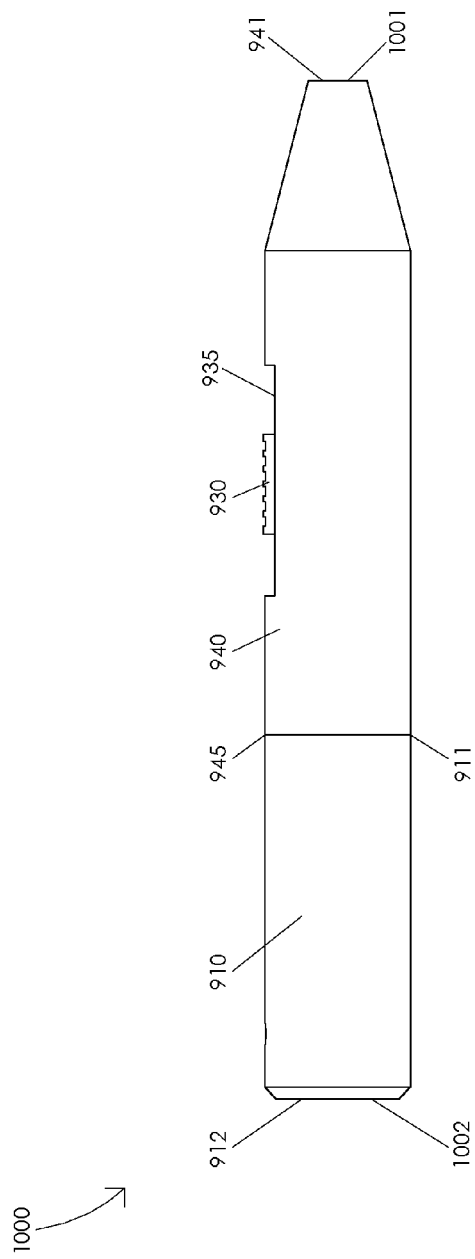
FIGS. 10A and 10B are schematic diagrams illustrating a handle.
Figure 10B:
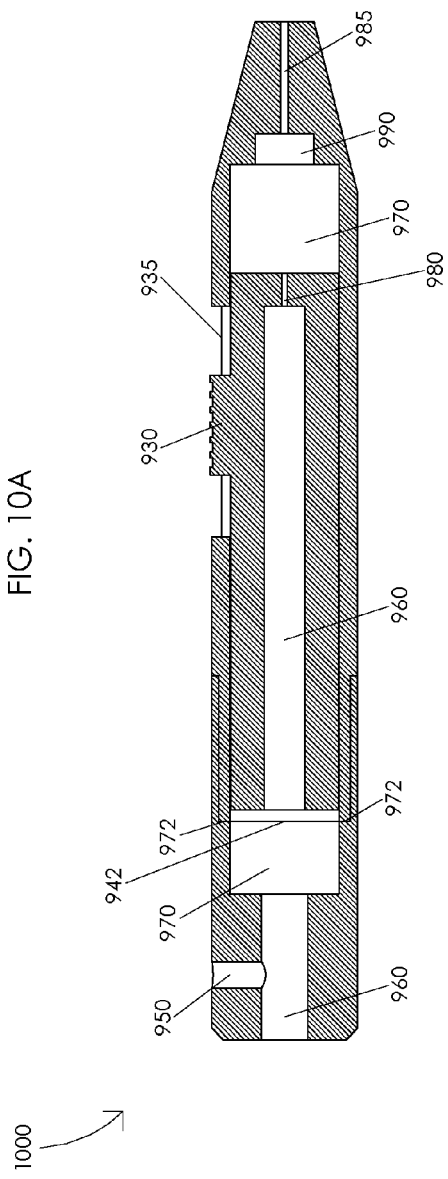

FIGS. 10A and 10B are schematic diagrams illustrating a handle 1000. FIG. 10A illustrates a side view of a handle 1000. In one or more embodiments, handle 1000 may comprise a handle distal end 1001 and a handle proximal end 1002. Illustratively, handle distal end 1001 may comprise handle base distal end 941. In one or more embodiments, handle proximal end 1002 may comprise outer cylinder proximal end 912. Illustratively, outer cylinder distal end 911 may be disposed adjacent to outer cylinder interface 945. In one or more embodiments, actuation control 930 may be disposed with actuation channel 935.

FIG. 10B illustrates a cross-sectional view of a handle 1000. In one or more embodiments, a portion of handle base 940 may be disposed within a portion of outer cylinder 910. Illustratively, a portion of handle base 940 may be disposed within handle base housing 971. In one or more embodiments, a portion of handle base 940 may be disposed within handle base housing 971 wherein handle base proximal end 942 may be disposed adjacent to handle base interface 972. Illustratively, actuation mechanism 920 may be disposed within actuation mechanism guide 970. In one or more embodiments, actuation mechanism 920 may be configured to actuate within actuation mechanism guide 970. Illustratively, actuation control 930 may be configured to control an actuation of actuation mechanism 920, e.g., within actuation mechanism guide 970.

In one or more embodiments, an actuation of actuation control 930 within actuation channel 935 may be configured to actuate actuation mechanism 920 within actuation mechanism guide 970. Illustratively, an actuation of actuation control distal end 931 towards actuation channel distal end 936 may be configured to actuate actuation mechanism distal end 921 towards handle distal end 1001. In one or more embodiments, an actuation of actuation control proximal end 932 towards actuation channel proximal end 937 may be configured to actuate actuation mechanism proximal end 922 towards handle proximal end 1002. Illustratively, a pressure mechanism, e.g., a spring, may be disposed within pressure mechanism housing 990. In one or more embodiments, a pressure mechanism may be configured to resist an actuation of actuation mechanism distal end 921 towards handle distal end 1001. Illustratively, a pressure mechanism may be configured to facilitate an actuation of actuation mechanism proximal end 922 towards handle proximal end 1002.

Figure 11C:
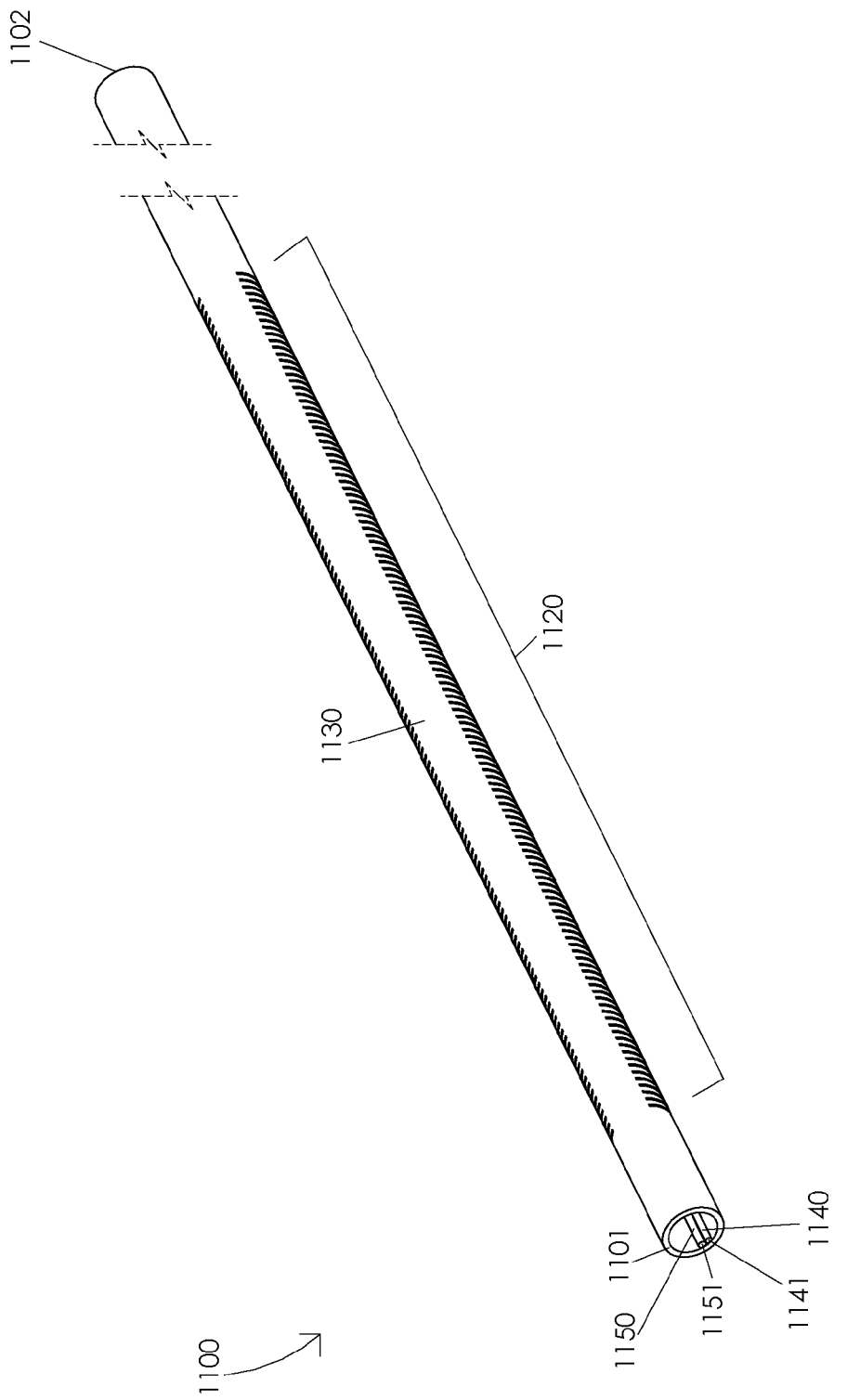

FIGS. 11A, 11B, and 11C are schematic diagrams illustrating a housing tube 1100. In one or more embodiments, housing tube 1100 may comprise a housing tube distal end 1101 and a housing tube proximal end 1102. Housing tube 1100 may be manufactured from any suitable material, e.g., polymers, metals, metal alloys, etc., or from any combination of suitable materials. FIG. 11A illustrates a housing tube 1100 oriented to illustrate a first housing tube portion 1120. Illustratively, first housing tube portion 1120 may have a first stiffness. FIG. 11B illustrates a housing tube 1100 oriented to illustrate a second housing tube portion 1130. Illustratively, second housing tube portion 1130 may have a second stiffness. In one or more embodiments, the second stiffness may be greater than the first stiffness. Illustratively, first housing tube portion 1120 may comprise a first material having a first stiffness. In one or more embodiments, second housing tube portion 1130 may comprise a second material having a second stiffness. Illustratively, the second stiffness may be greater than the first stiffness.

In one or more embodiments, housing tube 1100 may comprise a non-uniform inner diameter or a non-uniform outer diameter, e.g., to vary a stiffness of one or more portions of housing tube 1100. Illustratively, a first housing tube portion 1120 may comprise a first inner diameter of housing tube 1100 and a second housing tube portion 1130 may comprise a second inner diameter of housing tube 1100. In one or more embodiments, the first inner diameter of housing tube 1100 may be larger than the second inner diameter of housing tube 1100. Illustratively, a first housing tube portion 1120 may comprise a first outer diameter of housing tube 1100 and a second housing tube portion 1130 may comprise a second outer diameter of housing tube 1100. In one or more embodiments, the first outer diameter of housing tube 1100 may be smaller than the second outer diameter of housing tube 1100.

In one or more embodiments, first housing tube portion 1120 may comprise one or more apertures configured to produce a first stiffness of first housing tube portion 1120. Illustratively, second housing tube portion 1130 may comprise a solid portion of housing tube 1100 having a second stiffness. In one or more embodiments, the second stiffness may be greater than the first stiffness. Illustratively, first housing tube portion 1120 may comprise one or more apertures configured to produce a first stiffness of first housing tube portion 1120. In one or more embodiments, second housing tube portion 1130 may comprise one or more apertures configured to produce a second stiffness of second housing tube portion 1130. Illustratively, the second stiffness may be greater than the first stiffness.

In one or more embodiments, first housing tube portion 1120 may comprise a plurality of slits configured to separate one or more solid portions of housing tube 1100. Illustratively, a plurality of slits may be cut, e.g., laser cut, into first housing tube portion 1120. In one or more embodiments, first housing tube portion 1120 may comprise a plurality of slits configured to minimize a force of friction between housing tube 1100 and a cannula, e.g., as housing tube 1100 is inserted into the cannula or as housing tube 1100 is extracted from the cannula. For example, each slit of the plurality of slits may comprise one or more arches configured to minimize a force of friction between housing tube 1100 and a cannula.

FIG. 11C illustrates an angled view of housing tube 1100. Illustratively, an optic fiber 1150 may be disposed within housing tube 1100. In one or more embodiments, optic fiber 1150 may be disposed within housing tube 1100 wherein an optic fiber distal end 1151 is adjacent to housing tube distal end 1101. Illustratively, optic fiber 1150 may be disposed within housing tube 1100 wherein a portion of optic fiber 1150 may be adjacent to a portion of first housing tube portion 1120. In one or more embodiments, a portion of optic fiber 1150 may be fixed to an inner portion of housing tube 1100, e.g., by a biocompatible adhesive or any other suitable means.

Illustratively, a wire 1140 may be disposed within housing tube 1100. In one or more embodiments, wire 1140 may be disposed within housing tube 1100 wherein a wire distal end 1141 may be adjacent to housing tube distal end 1101. Illustratively, wire 1140 may be disposed within housing tube 1100 wherein a portion of wire 1140 may be adjacent to a portion of first housing tube portion 1120. In one or more embodiments, a portion of wire 1140 may be fixed to an inner portion of housing tube 1100, e.g., by a biocompatible adhesive or any other suitable fixation means.

Figure 12:
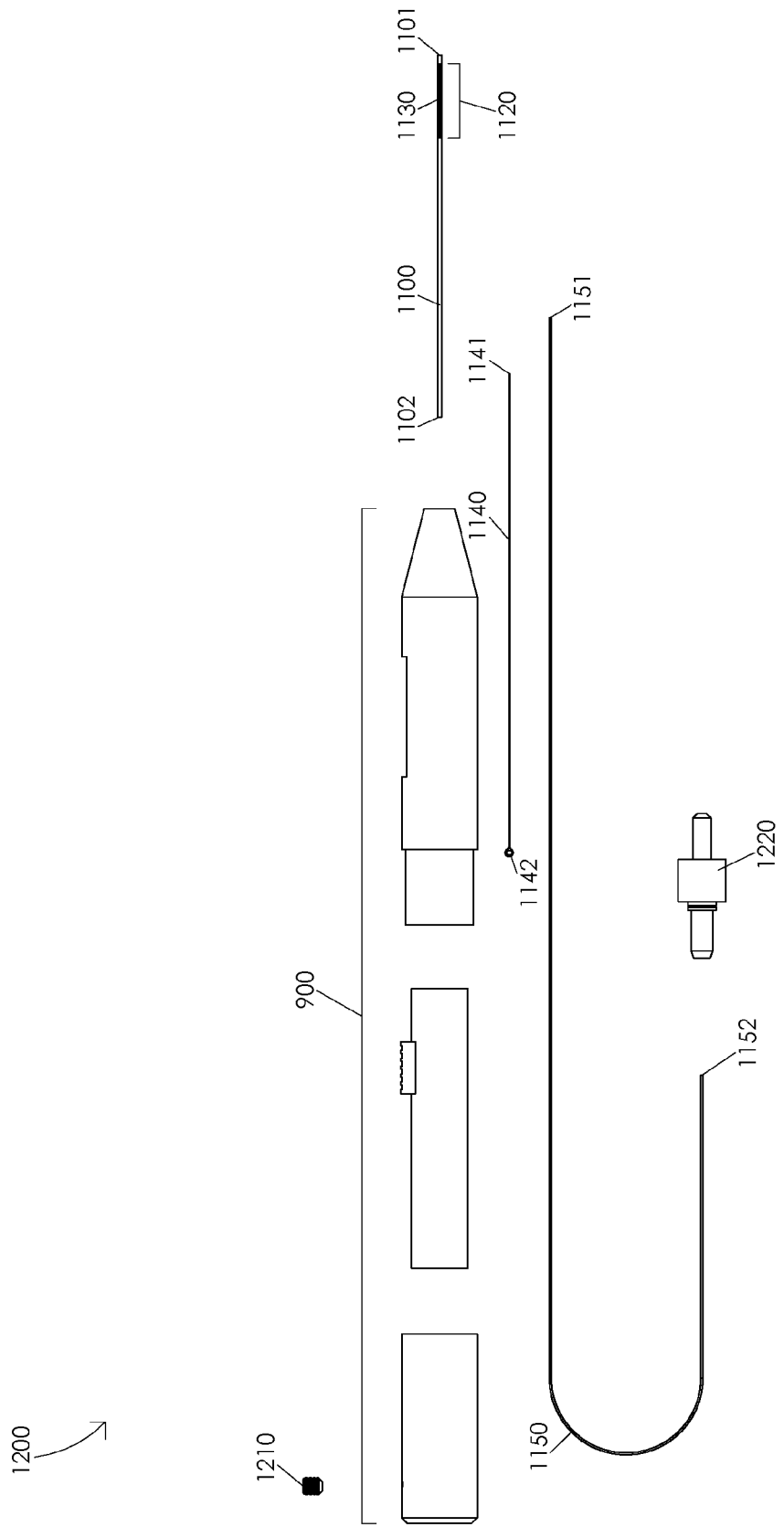
FIG. 12 is a schematic diagram illustrating an exploded view of a steerable laser probe assembly.

FIG. 12 is a schematic diagram illustrating an exploded view of a steerable laser probe assembly 1200. In one or more embodiments, a steerable laser probe assembly 1200 may comprise a handle assembly 900, a housing tube 1100 having a housing tube distal end 1101 and a housing tube proximal end 1102, a wire 1140 having a wire distal end 1141 and a wire proximal loop 1142, an optic fiber 1150 having an optic fiber distal end 1151 and an optic fiber proximal end 1152, a fixation mechanism 1210, and a light source interface 1220. Illustratively, light source interface 1220 may be configured to interface with optic fiber proximal end 1152. In one or more embodiments, light source interface 1220 may comprise a standard light source connector, e.g., an SMA connector.

Illustratively, housing tube 1100 may be disposed within housing tube housing 980 and housing tube guide 985. In one or more embodiments, housing tube 1100 may be fixed within housing tube housing 980, e.g., housing tube proximal end 1102 may be fixed within housing tube housing 980. Illustratively, housing tube 1100 may be fixed within housing tube housing 980, e.g., by an adhesive or by any suitable fixation means. In one or more embodiments, an actuation of actuation mechanism 920 may be configured to actuate housing tube 1100. Illustratively, actuation control 930 may be configured to control an actuation of housing tube 1100. In one or more embodiments, an actuation of actuation control 930 within actuation channel 935 may be configured to actuate housing tube 1100 relative to handle base 940. Illustratively, an actuation of actuation control distal end 931 towards actuation channel distal end 936 may be configured to extend housing tube 1100 relative to handle proximal end 1002. In one or more embodiments, an actuation of actuation control proximal end 932 towards actuation channel proximal end 937 may be configured to retract housing tube 1100 relative to handle proximal end 1002.

Illustratively, optic fiber 1150 may be disposed within inner bore 960, actuation mechanism guide 970, housing tube housing 980, housing tube guide 985, and housing tube 1100. In one or more embodiments, optic fiber 1150 may be disposed within housing tube 1100 wherein optic fiber distal end 1151 may be adjacent to housing tube distal end 1101. Illustratively, a portion of optic fiber 1150 may be fixed to an inner portion of housing tube 1100, e.g., by an adhesive or any suitable fixation means.

In one or more embodiments, wire 1140 may be disposed within fixation mechanism housing 950, inner bore 960, actuation mechanism guide 970, housing tube housing, housing tube guide 985, and housing tube 1100. Illustratively, a portion of wire 1140 may be fixed to an inner portion of housing tube 1100, e.g., by an adhesive or any suitable fixation means. In one or more embodiments, fixation mechanism 1210 may be disposed within fixation mechanism housing 950. Illustratively, fixation mechanism 1210 may be configured to fix wire 1140 in a position relative to handle 1000, e.g., at fixation mechanism housing 950. In one or more embodiments, fixation mechanism 1210 may comprise a set screw configured to fix wire 1140 in a position relative to handle 1000, e.g., by fixing wire proximal loop 1142 in a position within handle 1000. For example, wire proximal loop 1142 may be looped around fixation mechanism 1210, e.g., fixation mechanism 1210 may be disposed within wire proximal loop 1142. Illustratively, wire 1140 may be fixed to fixation mechanism 1210, e.g., by an adhesive or any suitable fixation means. For example, fixation mechanism 1210 may be configured to fix wire 1140 in a position relative to handle 1000, e.g., by an interference fit. Illustratively, wire 1140 may be fixed in a position relative to handle 1000, e.g., by fixation mechanism 1210, and wire 1140 may also be fixed to an inner portion of housing tube 1100, e.g., a first housing tube portion 1120.

In one or more embodiments, an actuation of actuation mechanism 920 may be configured to actuate housing tube 1100 relative to wire 1140. Illustratively, actuation control 930 may be configured to control an actuation of actuation mechanism 920 and housing tube 1100. In one or more embodiments, an actuation of actuation control distal end 931 towards actuation channel distal end 936 may be configured to actuate actuation mechanism distal end 921 towards handle distal end 1001. Illustratively, an actuation of actuation mechanism distal end 921 towards handle distal end 1001 may be configured to extend housing tube 1100 relative to wire 1140 and handle proximal end 1002. In one or more embodiments, an actuation of actuation control proximal end 932 towards actuation channel proximal end 937 may be configured to actuate actuation mechanism proximal end 922 towards handle proximal end 1002. Illustratively, an actuation of actuation mechanism proximal end 922 towards handle proximal end 1002 may be configured to retract housing tube 1100 relative to wire 1140 and handle proximal end 1002.

In one or more embodiments, wire 1140 may be configured to resist an extension of housing tube 1100 relative to handle proximal end 1002. Illustratively, wire 1140 may be fixed in a position relative to handle 1000, e.g., by fixation mechanism 1210, and a portion of wire 1140 may be fixed to an inner portion of housing tube 1100, e.g., a first housing tube portion 1120. In one or more embodiments, as housing tube 1100 is extended relative to handle proximal end 1002, e.g., due to an actuation of actuation mechanism distal end 921 towards handle distal end 1001, wire 1140 may be configured to resist the extension of housing tube 1100 relative to handle proximal end 1002. Illustratively, as housing tube 1100 is gradually extended relative to handle proximal end 1002, wire 1140 may be configured to gradually compress a portion of housing tube 1100, e.g., a first housing tube portion 1120, causing housing tube 1100 to gradually curve. In one or more embodiments, a gradual curving of housing tube 1100 may be configured to gradually curve optic fiber 1150.

Illustratively, a retraction of housing tube 1100 relative to handle proximal end 1002, e.g., due to an actuation of actuation mechanism proximal end 922 towards handle proximal end 1002, may be configured to reduce a compressive force applied, e.g., by wire 1140, to a portion of housing tube 1100. In one or more embodiments, a gradual retraction of housing tube 1100 relative to handle proximal end 1002 may be configured to gradually decompress a portion of housing tube 1100, e.g., a first housing tube portion 1120, causing housing tube 1100 to gradually straighten. Illustratively, a gradual straightening of housing tube 1100 may be configured to gradually straighten optic fiber 1150.

In one or more embodiments, an extension of actuation control 930 relative to handle proximal end 1002 may comprise an actuation of actuation control distal end 931 towards actuation channel distal end 936. Illustratively, actuation control 930 may be fully extended relative to handle proximal end 1002, e.g., when actuation control distal end 931 is adjacent to actuation channel distal end 936. In one or more embodiments, an extension of actuation mechanism 920 relative to handle proximal end 1002 may comprise an actuation of actuation mechanism distal end 921 towards handle distal end 1001. Illustratively, an extension of actuation control 930 relative to handle proximal end 1002 may be configured to cause an extension of actuation mechanism 920 relative to handle proximal end 1002. In one or more embodiments, an extension of actuation mechanism 920 relative to handle proximal end 1002 may be configured to extend housing tube 1100 relative to handle proximal end 1002 and wire 1140. Illustratively, an extension of housing tube 1100 relative to wire 1140 may be configured to curve housing tube 1100. In one or more embodiments, a curving of housing tube 1100 may be configured to curve optic fiber 1150.

In one or more embodiments, a retraction of actuation control 930 relative to handle proximal end 1002 may comprise an actuation of actuation control proximal end 932 towards actuation channel proximal end 937. Illustratively, actuation control 930 may be fully retracted relative to handle proximal end 1002, e.g., when actuation control proximal end 932 is adjacent to actuation channel proximal end 937. In one or more embodiments, a retraction of actuation mechanism 920 relative to handle proximal end 1002 may comprise an actuation of actuation mechanism proximal end 922 towards handle proximal end 1002. Illustratively, a retraction of actuation control 930 relative to handle proximal end 1002 may be configured to cause a retraction of actuation mechanism 920 relative to handle proximal end 1002. In one or more embodiments, a retraction of actuation mechanism 920 relative to handle proximal end 1002 may be configured to retract housing tube 1100 relative to handle proximal end 1002 and wire 1140. Illustratively, a retraction of housing tube 1100 relative to wire 1140 may be configured to straighten housing tube 1100. In one or more embodiments, a straightening of housing tube 1100 may be configured to straighten optic fiber 1150.

Figure 13A:
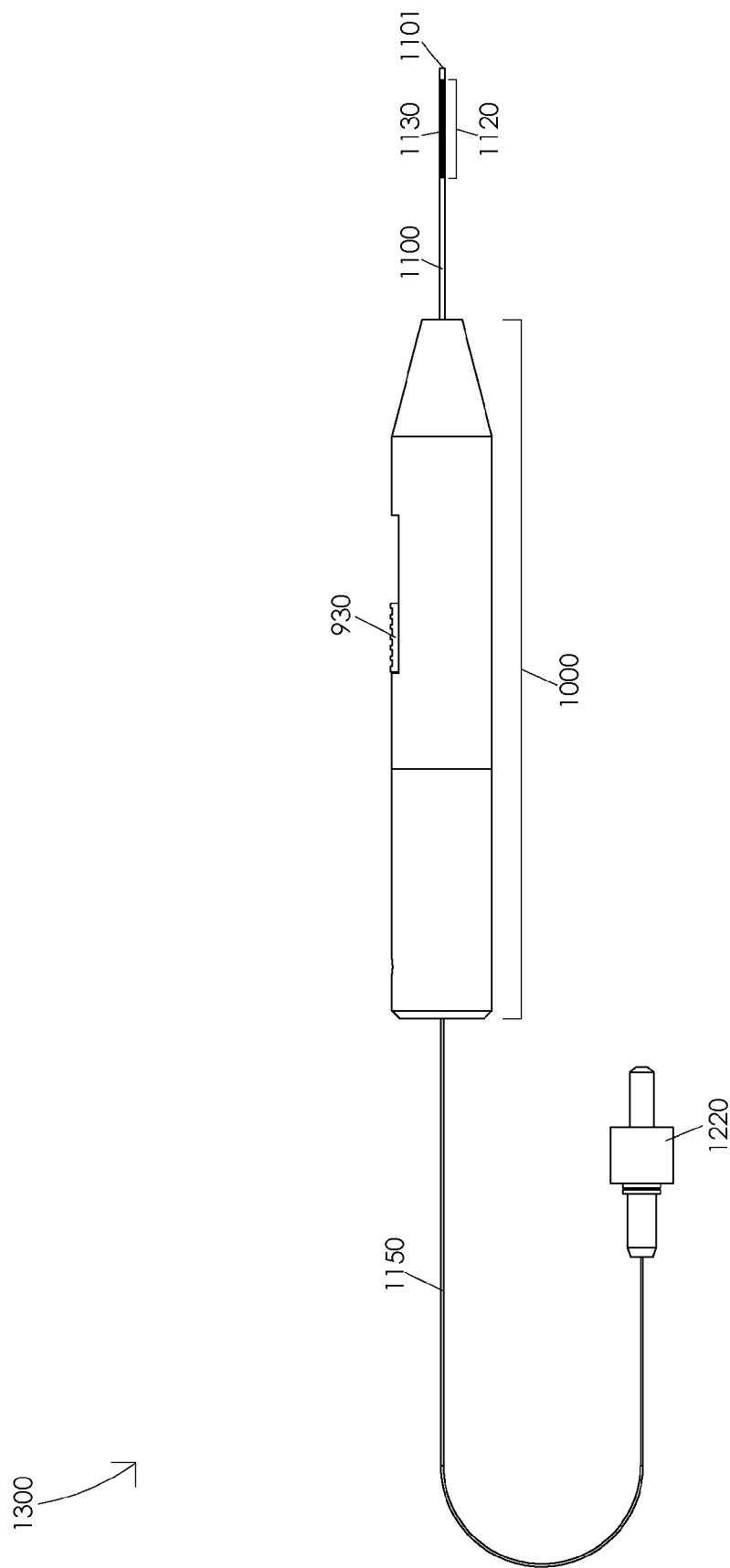
FIGS. 13A, 13B, 13C, 13D, and 13E illustrate a gradual curving of an optic fiber.

FIGS. 13A, 13B, 13C, 13D, and 13E illustrate a gradual curving of an optic fiber 1150. FIG. 13A illustrates a straight optic fiber 1300. In one or more embodiments, optic fiber 1150 may comprise a straight optic fiber 1300, e.g., when actuation control 930 is fully retracted relative to handle proximal end 1002. Illustratively, optic fiber 1150 may comprise a straight optic fiber 1300, e.g., when first housing tube portion 1120 is fully decompressed. In one or more embodiments, a line tangent to optic fiber distal end 1151 may be parallel to a line tangent to housing tube proximal end 1102, e.g., when optic fiber 1150 comprises a straight optic fiber 1300.

Figure 13B:
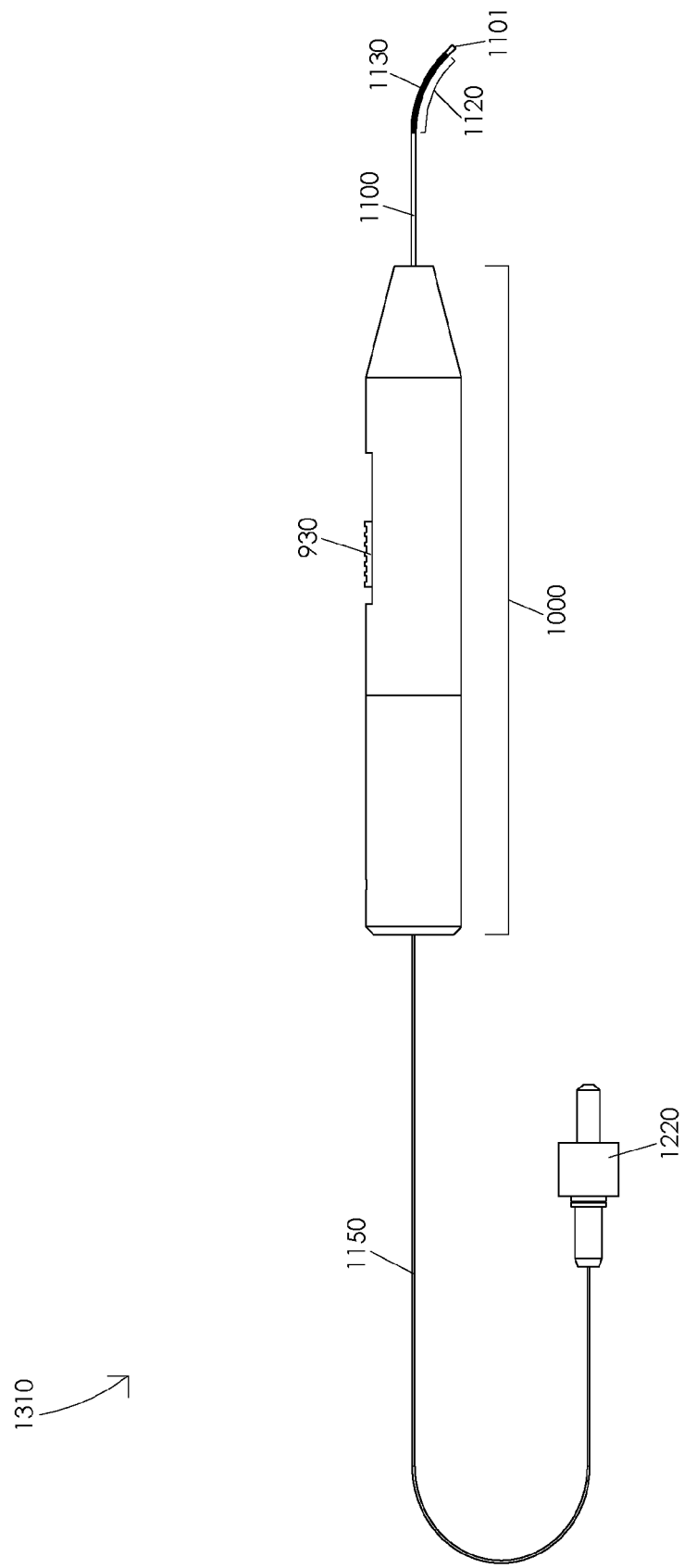

FIG. 13B illustrates an optic fiber in a first curved position 1310. Illustratively, an extension of actuation control 930 relative to handle proximal end 1002 may be configured to extend housing tube 1100 relative to wire 1140. In one or more embodiments, an extension of housing tube 1100 relative to wire 1140 may be configured to cause wire 1140 to compress a portion of housing tube 1100 causing housing tube 1100 to gradually curve. Illustratively, a gradual curving of housing tube 1100 may be configured to gradually curve optic fiber 1150. In one or more embodiments, an extension of actuation control 930 relative to handle proximal end 1002 may be configured to gradually curve optic fiber 1150 from a straight optic fiber 1300 to an optic fiber in a first curved position 1310. Illustratively, an extension of actuation mechanism 920 relative to handle proximal end 1002 may be configured to extend housing tube 1100 relative to wire 1140. In one or more embodiments, an extension of housing tube 1100 relative to wire 1140 may be configured to gradually curve optic fiber 1150 from a straight optic fiber 1300 to an optic fiber in a first curved position 1310. Illustratively, a line tangent to optic fiber distal end 1151 may intersect a line tangent to housing tube proximal end 1102 at a first angle, e.g., when optic fiber 1150 comprises an optic fiber in a first curved position 1310. In one or more embodiments, the first angle may comprise any angle greater than zero degrees. For example, the first angle may comprise a 45 degree angle.

Figure 13C:
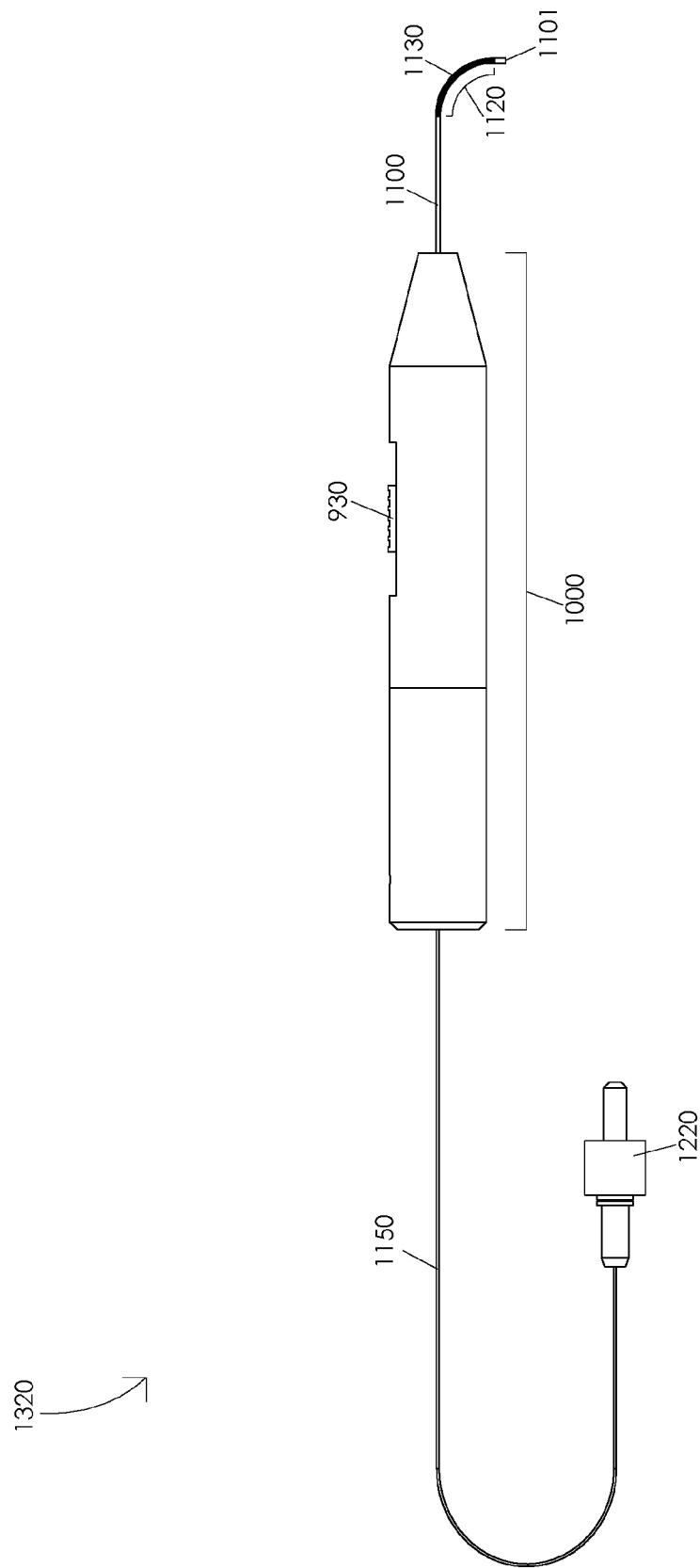

FIG. 13C illustrates an optic fiber in a second curved position 1320. Illustratively, an extension of actuation control 930 relative to handle proximal end 1002 may be configured to extend housing tube 1100 relative to wire 1140. In one or more embodiments, an extension of housing tube 1100 relative to wire 1140 may be configured to cause wire 1140 to compress a portion of housing tube 1100 causing housing tube 1100 to gradually curve. Illustratively, a gradual curving of housing tube 1100 may be configured to gradually curve optic fiber 1150. In one or more embodiments, an extension of actuation control 930 relative to handle proximal end 1002 may be configured to gradually curve optic fiber 1150 from an optic fiber in a first curved position 1310 to an optic fiber in a second curved position 1320. Illustratively, an extension of actuation mechanism 920 relative to handle proximal end 1002 may be configured to extend housing tube 1100 relative to wire 1140. In one or more embodiments, an extension of housing tube 1100 relative to wire 1140 may be configured to gradually curve optic fiber 1150 from an optic fiber in a first curved position 1310 to an optic fiber in a second curved position 1320. Illustratively, a line tangent to optic fiber distal end 1151 may intersect a line tangent to housing tube proximal end 1102 at a second angle, e.g., when optic fiber 1150 comprises an optic fiber in a second curved position 1320. In one or more embodiments, the second angle may comprise any angle greater than the first angle. For example, the second angle may comprise a 90 degree angle.

Figure 13D:
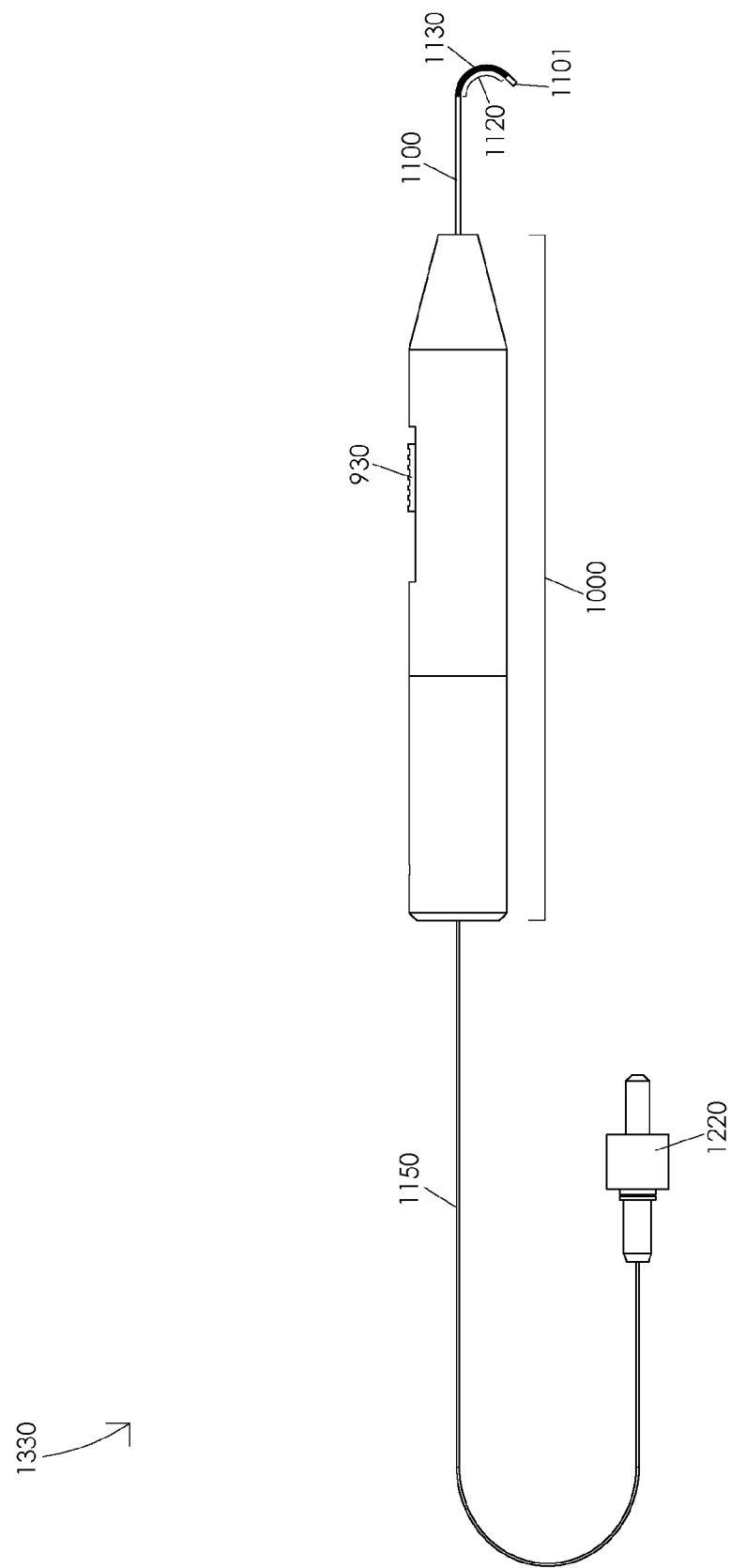

FIG. 13D illustrates an optic fiber in a third curved position 1330. Illustratively, an extension of actuation control 930 relative to handle proximal end 1002 may be configured to extend housing tube 1100 relative to wire 1140. In one or more embodiments, an extension of housing tube 1100 relative to wire 1140 may be configured to cause wire 1140 to compress a portion of housing tube 1100 causing housing tube 1100 to gradually curve. Illustratively, a gradual curving of housing tube 1100 may be configured to gradually curve optic fiber 1150. In one or more embodiments, an extension of actuation control 930 relative to handle proximal end 1002 may be configured to gradually curve optic fiber 1150 from an optic fiber in a second curved position 1320 to an optic fiber in a third curved position 1330. Illustratively, an extension of actuation mechanism 920 relative to handle proximal end 1002 may be configured to extend housing tube 1100 relative to wire 1140. In one or more embodiments, an extension of housing tube 1100 relative to wire 1140 may be configured to gradually curve optic fiber 1150 from an optic fiber an optic fiber in a second curved position 1320 to an optic fiber in a third curved position 1330. Illustratively, a line tangent to optic fiber distal end 1151 may intersect a line tangent to housing tube proximal end 1102 at a third angle, e.g., when optic fiber 1150 comprises an optic fiber in a third curved position 1330. In one or more embodiments, the third angle may comprise any angle greater than the second angle. For example, the third angle may comprise a 135 degree angle.

Figure 13E:
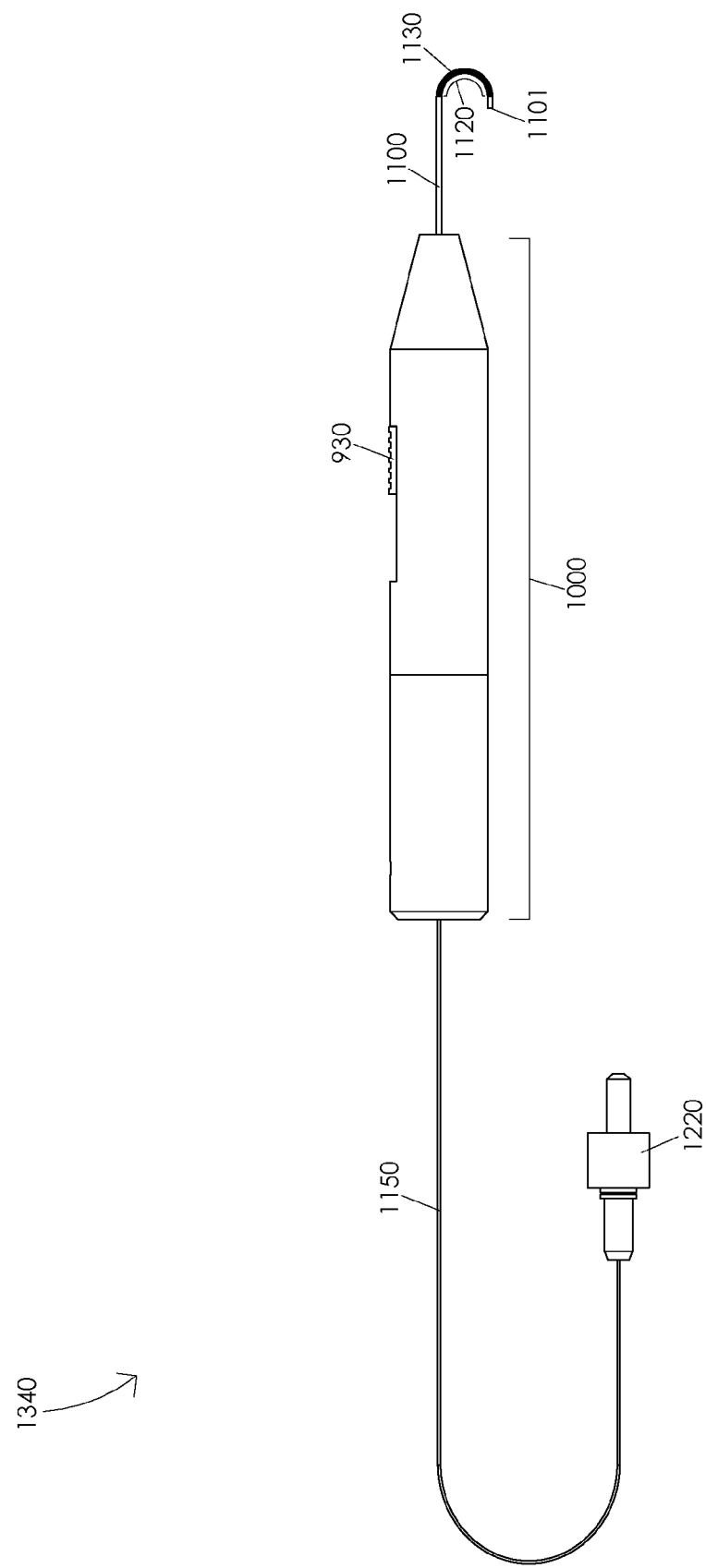

FIG. 13E illustrates an optic fiber in a fourth curved position 1340. Illustratively, an extension of actuation control 930 relative to handle proximal end 1002 may be configured to extend housing tube 1100 relative to wire 1140. In one or more embodiments, an extension of housing tube 1100 relative to wire 1140 may be configured to cause wire 1140 to compress a portion of housing tube 1100 causing housing tube 1100 to gradually curve. Illustratively, a gradual curving of housing tube 1100 may be configured to gradually curve optic fiber 1150. In one or more embodiments, an extension of actuation control 930 relative to handle proximal end 1002 may be configured to gradually curve optic fiber 1150 from an optic fiber in a third curved position 1330 to an optic fiber in a fourth curved position 1340. Illustratively, an extension of actuation mechanism 920 relative to handle proximal end 1002 may be configured to extend housing tube 1100 relative to wire 1140. In one or more embodiments, an extension of housing tube 1100 relative to wire 1140 may be configured to gradually curve optic fiber 1150 from an optic fiber an an optic fiber in a third curved position 1330 to an optic fiber in a fourth curved position 1340. For example, a line tangent to optic fiber distal end 1151 may be parallel to a line tangent to housing tube proximal end 1102, e.g., when optic fiber 1150 comprises an optic fiber in a fourth curved position 1340.

In one or more embodiments, one or more properties of a steerable laser probe may be adjusted to attain one or more desired steerable laser probe features. For example, a stiffness of first housing tube portion 1120 or a stiffness of second housing tube portion 1130 may be adjusted to vary an amount of actuation of actuation mechanism 920 configured to curve housing tube 1100 to a particular curved position. Illustratively, a material comprising first housing tube portion 1120 or a material comprising second housing tube portion 1130 may be adjusted to vary an amount of actuation of actuation mechanism 920 configured to curve housing tube 1100 to a particular curved position. In one or more embodiments, an inner diameter of first housing tube portion 1120 or an inner diameter of second housing tube portion 1130 may be adjusted to vary an amount of actuation structure 920 configured to curve housing tube 1100 to a particular curved position. Illustratively, an outer diameter of first housing tube portion 1120 or an outer diameter of second housing tube portion 1130 may be adjusted to vary an amount of actuation structure 920 configured to curve housing tube 1100 to a particular curved position.

In one or more embodiments, a number of apertures in housing tube 1100 may be adjusted to vary an amount of actuation of actuation mechanism 920 configured to curve housing tube 1100 to a particular curved position. Illustratively, a location of one or more apertures in housing tube 1100 may be adjusted to vary an amount of actuation of actuation mechanism 920 configured to curve housing tube 1100 to a particular curved position. In one or more embodiments, a geometry of one or more apertures in housing tube 1100 may be adjusted to vary an amount of actuation of actuation mechanism 920 configured to curve housing tube 1100 to a particular curved position. Illustratively, a geometry of one or more apertures in housing tube 1100 may be uniform, e.g., each aperture of the one or more apertures may have a same geometry. In one or more embodiments, a geometry of one or more apertures in housing tube 1100 may be non-uniform, e.g., a first aperture in housing tube 1100 may have a first geometry and a second aperture in housing tube 1100 may have a second geometry.

Illustratively, a geometry or shape of actuation mechanism 920 may be adjusted to vary an amount actuation of actuation mechanism 920 configured to curve housing tube 1100 to a particular curved position. In one or more embodiments, one or more locations within housing tube 1100 wherein wire 1140 may be fixed to an inner portion of housing tube 1100 may be adjusted to vary an amount of actuation of actuation mechanism 920 configured to curve housing tube 1100 to a particular curved position. Illustratively, at least a portion of optic fiber 1150 may be enclosed in an optic fiber sleeve configured to, e.g., protect optic fiber 1150, vary a stiffness of optic fiber 1150, vary an optical property of optic fiber 1150, etc. In one or more embodiments, a portion of optic fiber 1150 that may be fixed to an inner portion of housing tube 1100 may be enclosed in an optic fiber sleeve configured to, e.g., protect optic fiber 1150, facilitate a fixation, etc. Illustratively, a portion of housing tube 1100 may comprise an access window, e.g., configured to allow access to an inner portion of housing tube 1100. In one or more embodiments, a portion of housing tube 1100 may comprise an access window, e.g., configured to allow access to a portion of wire 1140 or a portion of optic fiber 1150.

Illustratively, a stiffness of first housing tube portion 1120 or a stiffness of second housing tube portion 1130 may be adjusted to vary a bend radius of housing tube 1100. In one or more embodiments, a stiffness of first housing tube portion 1120 or a stiffness of second housing tube portion 1130 may be adjusted to vary a radius of curvature of housing tube 1100, e.g., when housing tube 1100 is in a particular curved position. Illustratively, a number of apertures in housing tube 1100 may be adjusted to vary a bend radius of housing tube 1100. In one or more embodiments, a number of apertures in housing tube 1100 may be adjusted to vary a radius of curvature of housing tube 1100, e.g., when housing tube 1100 is in a particular curved position. Illustratively, a location or a geometry of one or more apertures in housing tube 1100 may be adjusted to vary a bend radius of housing tube 1100. In one or more embodiments, a location or a geometry of one or more apertures in housing tube 1100 may be adjusted to vary a radius of curvature of housing tube 1100, e.g., when housing tube 1100 is in a particular curved position.

Figure 14A:
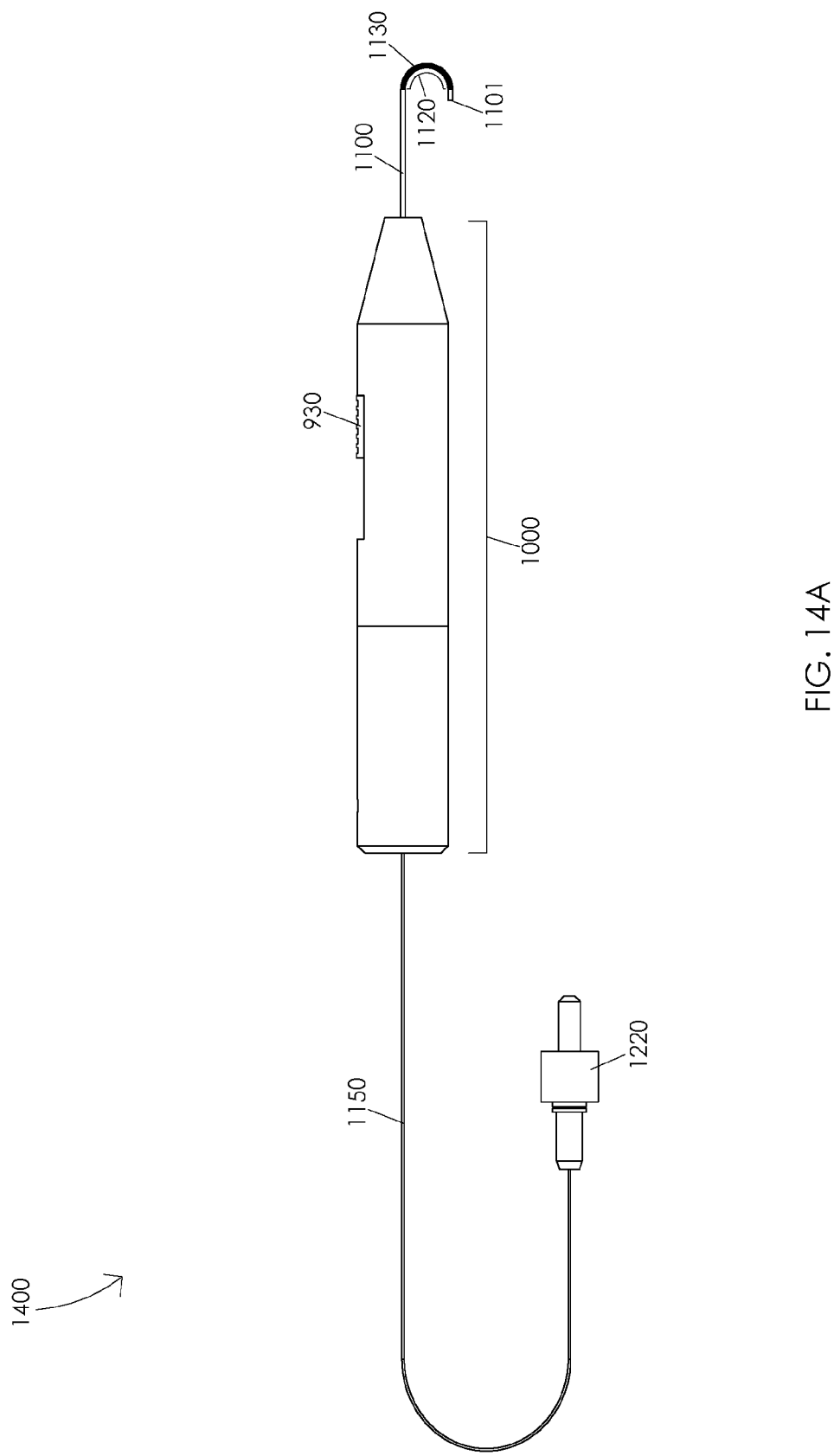
FIGS. 14A, 14B, 14C, 14D, and 14E illustrate a gradual straightening of an optic fiber.

FIGS. 14A, 14B, 14C, 14D, and 14E illustrate a gradual straightening of an optic fiber 1150. FIG. 14A illustrates a fully curved optic fiber 1400. In one or more embodiments, optic fiber 1150 may comprise a fully curved optic fiber 1400, e.g., when actuation control 930 is fully extended relative to handle proximal end 1002. Illustratively, optic fiber 1150 may comprise a fully curved optic fiber 1400, e.g., when first housing tube portion 1120 is fully compressed. In one or more embodiments, a line tangent to optic fiber distal end 1151 may be parallel to a line tangent to housing tube proximal end 1102, e.g., when optic fiber 1150 comprises a straight optic fiber 1400.

Figure 14B:
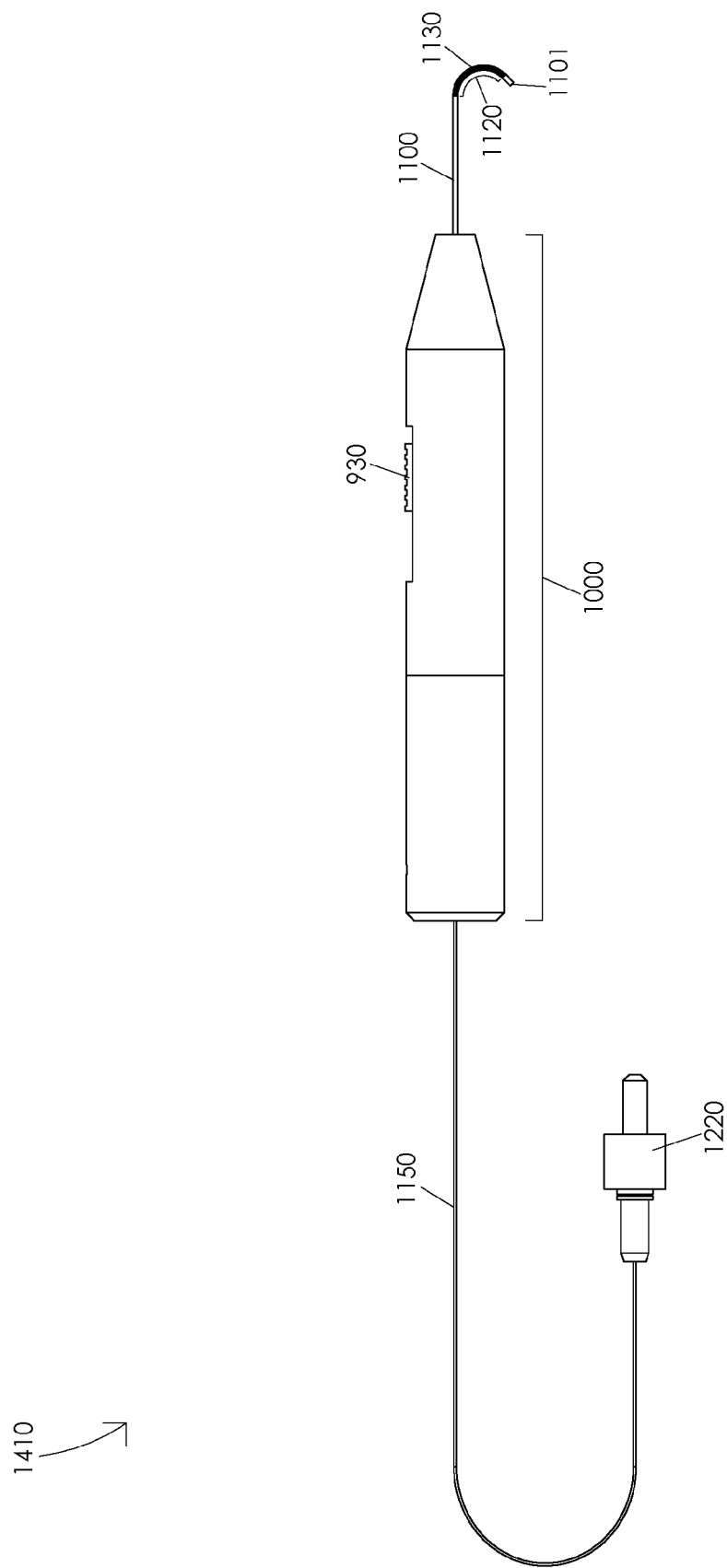

FIG. 14B illustrates an optic fiber in a first partially straightened position 1410. Illustratively, a retraction of actuation control 930 relative to handle proximal end 1002 may be configured to retract housing tube 1100 relative to wire 1140. In one or more embodiments, a retraction of housing tube 1100 relative to wire 1140 may be configured to cause wire 1140 to decompress a portion of housing tube 1100, e.g., a first housing tube portion 1120, causing housing tube 1100 to gradually straighten. Illustratively, a gradual straightening of housing tube 1100 may be configured to gradually straighten optic fiber 1150. In one or more embodiments, a retraction of actuation control 930 relative to handle proximal end 1002 may be configured to gradually straighten optic fiber 1150 from a fully curved optic fiber 1400 to an optic fiber in a first partially straightened position 1410. Illustratively, a retraction of actuation mechanism 920 relative to handle proximal end 1002 may be configured to retract housing tube 1100 relative to wire 1140. In one or more embodiments, a retraction of housing tube 1100 relative to wire 1140 may be configured to gradually straighten optic fiber 1150 from a fully curved optic fiber 1400 to an optic fiber in a first partially straightened position 1410. Illustratively, a line tangent to optic fiber distal end 1151 may intersect a line tangent to housing tube proximal end 1102 at a first partially straightened angle, e.g., when optic fiber 1150 comprises an optic fiber in a first partially straightened position 1410. Illustratively, the first partially straightened angle may comprise any angle less than 180 degrees. For example, the first partially straightened angle may comprise a 135 degree angle.

Figure 14C:
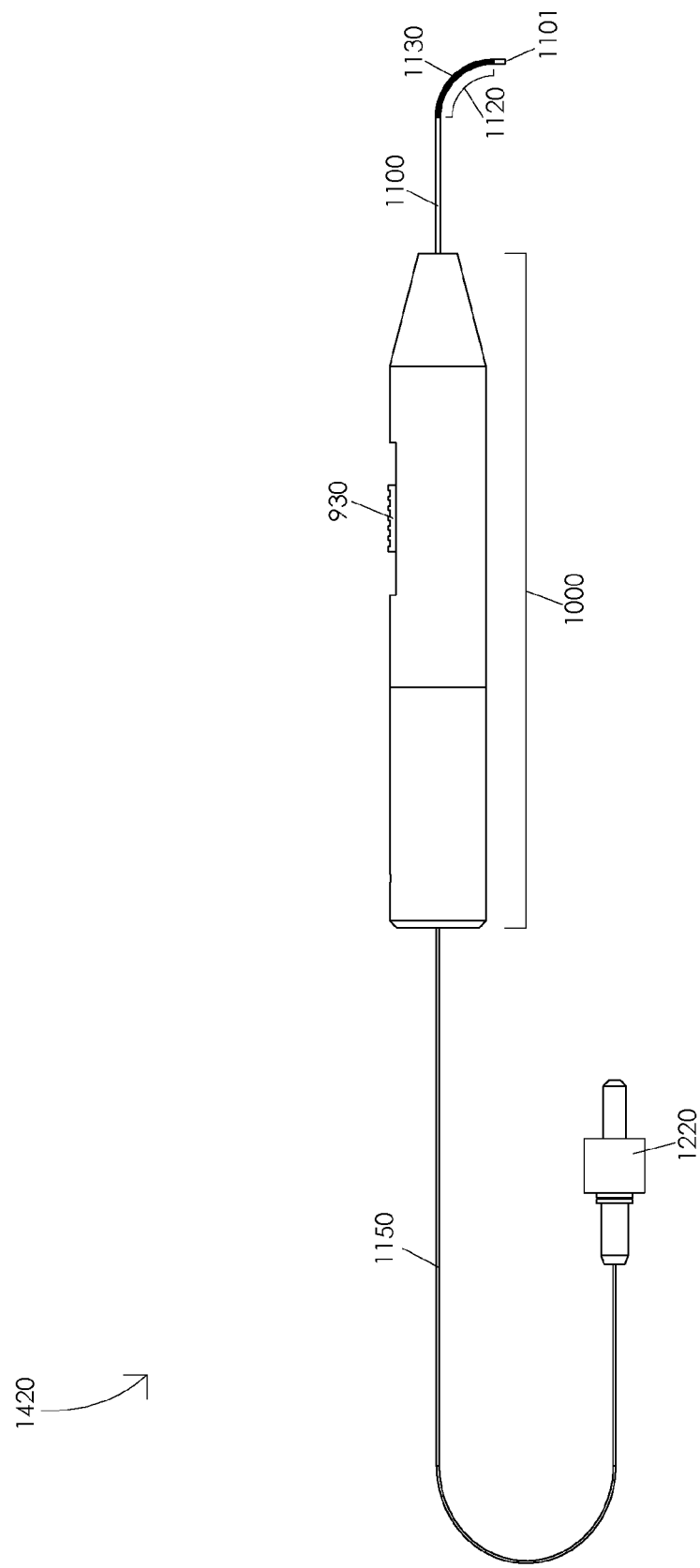

FIG. 14C illustrates an optic fiber in a second partially straightened position 1420. Illustratively, a retraction of actuation control 930 relative to handle proximal end 1002 may be configured to retract housing tube 1100 relative to wire 1140. In one or more embodiments, a retraction of housing tube 1100 relative to wire 1140 may be configured to cause wire 1140 to decompress a portion of housing tube 1100, e.g., a first housing tube portion 1120, causing housing tube 1100 to gradually straighten. Illustratively, a gradual straightening of housing tube 1100 may be configured to gradually straighten optic fiber 1150. In one or more embodiments, a retraction of actuation control 930 relative to handle proximal end 1002 may be configured to gradually straighten optic fiber 1150 from an optic fiber in a first partially straightened position 1410 to an optic fiber in a second partially straightened position 1420. Illustratively, a retraction of actuation mechanism 920 relative to handle proximal end 1002 may be configured to retract housing tube 1100 relative to wire 1140. In one or more embodiments, a retraction of housing tube 1100 relative to wire 1140 may be configured to gradually straighten optic fiber 1150 from an optic fiber in a first partially straightened position 1410 to an optic fiber in a second partially straightened position 1420. Illustratively, a line tangent to optic fiber distal end 1151 may intersect a line tangent to housing tube proximal end 1102 at a second partially straightened angle, e.g., when optic fiber 1150 comprises an optic fiber in a second partially straightened position 1420. Illustratively, the second partially straightened angle may comprise any angle less than the first partially straightened angle. For example, the second partially straightened angle may comprise a 90 degree angle.

Figure 14D:
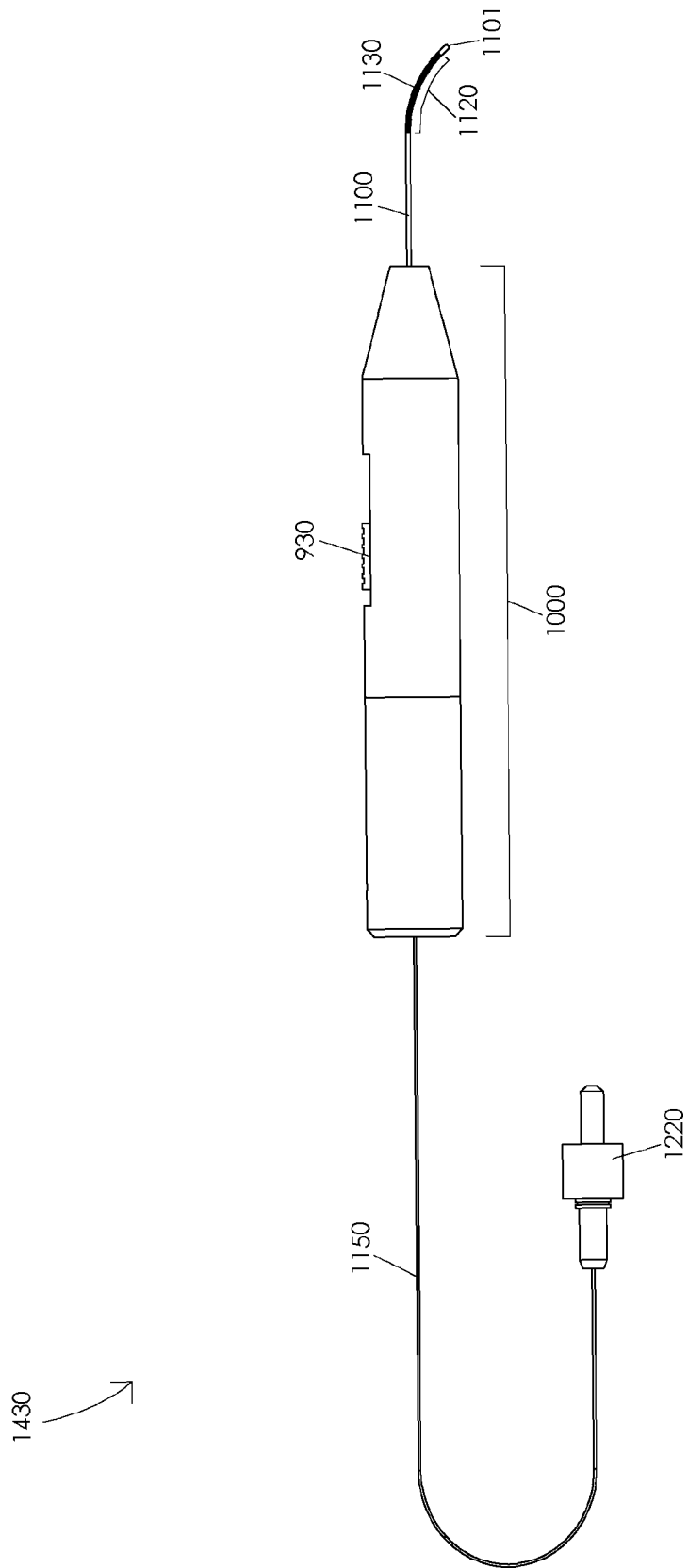

FIG. 14D illustrates an optic fiber in a third partially straightened position 1430. Illustratively, a retraction of actuation control 930 relative to handle proximal end 1002 may be configured to retract housing tube 1100 relative to wire 1140. In one or more embodiments, a retraction of housing tube 1100 relative to wire 1140 may be configured to cause wire 1140 to decompress a portion of housing tube 1100, e.g., a first housing tube portion 1120, causing housing tube 1100 to gradually straighten. Illustratively, a gradual straightening of housing tube 1100 may be configured to gradually straighten optic fiber 1150. In one or more embodiments, a retraction of actuation control 930 relative to handle proximal end 1002 may be configured to gradually straighten optic fiber 1150 from an optic fiber in a second partially straightened position 1420 to an optic fiber in a third partially straightened position 1430. Illustratively, a retraction of actuation mechanism 920 relative to handle proximal end 1002 may be configured to retract housing tube 1100 relative to wire 1140. In one or more embodiments, a retraction of housing tube 1100 relative to wire 1140 may be configured to gradually straighten optic fiber 1150 from an optic fiber in a second partially straightened position 1420 to an optic fiber in a third partially straightened position 1430. Illustratively, a line tangent to optic fiber distal end 1151 may intersect a line tangent to housing tube proximal end 1102 at a third partially straightened angle, e.g., when optic fiber 1150 comprises an optic fiber in a third partially straightened position 1430. Illustratively, the third partially straightened angle may comprise any angle less than the second partially straightened angle. For example, the third partially straightened angle may comprise a 45 degree angle.

Figure 14E:
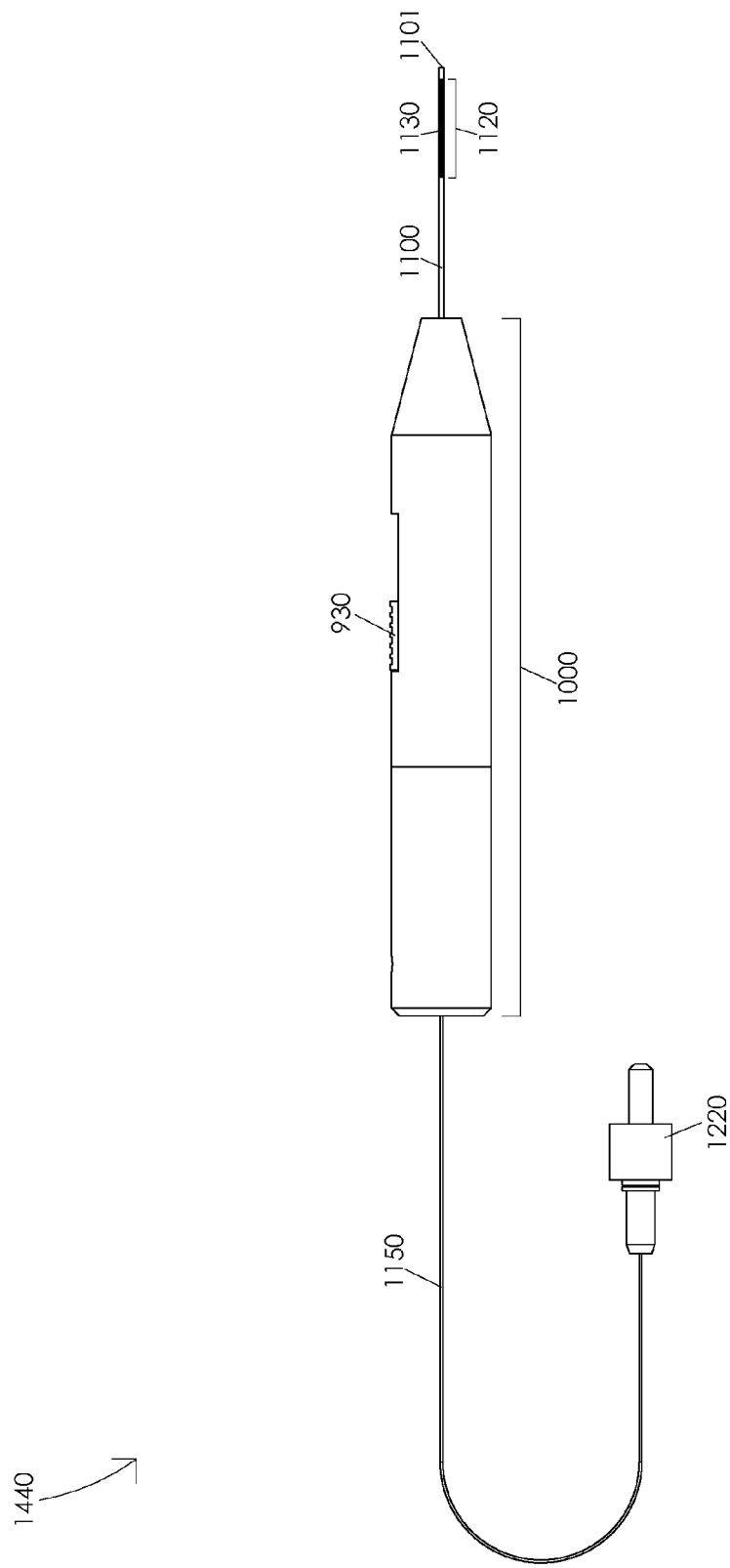

FIG. 14E illustrates an optic fiber in a fully straightened position 1440. Illustratively, a retraction of actuation control 930 relative to handle proximal end 1002 may be configured to retract housing tube 1100 relative to wire 1140. In one or more embodiments, a retraction of housing tube 1100 relative to wire 1140 may be configured to cause wire 1140 to decompress a portion of housing tube 1100, e.g., a first housing tube portion 1120, causing housing tube 1100 to gradually straighten. Illustratively, a gradual straightening of housing tube 1100 may be configured to gradually straighten optic fiber 1150. In one or more embodiments, a retraction of actuation control 930 relative to handle proximal end 1002 may be configured to gradually straighten optic fiber 1150 from an optic fiber in a third partially straightened position 1430 to an optic fiber in a fully straightened position 1440. Illustratively, a retraction of actuation mechanism 920 relative to handle proximal end 1002 may be configured to retract housing tube 1100 relative to wire 1140. In one or more embodiments, a retraction of housing tube 1100 relative to wire 1140 may be configured to gradually straighten optic fiber 1150 from an optic fiber in a third partially straightened position 1430 to an optic fiber in a fully straightened position 1440. Illustratively, a line tangent to optic fiber distal end 1151 may be parallel to a line tangent to housing tube proximal end 1102, e.g., when optic fiber 1150 comprises an optic fiber in a fully straightened position 1440.

Illustratively, a surgeon may aim optic fiber distal end 1151 at any of a plurality of targets within an eye, e.g., to perform a photocoagulation procedure. In one or more embodiments, a surgeon may aim optic fiber distal end 1151 at any target within a particular transverse plane of the inner eye by, e.g., rotating handle 1000 to orient housing tube 1100 in an orientation configured to cause a curvature of housing tube 1100 within the particular transverse plane of the inner eye and varying an amount of actuation of actuation mechanism 920. Illustratively, a surgeon may aim optic fiber distal end 1151 at any target within a particular sagittal plane of the inner eye by, e.g., rotating handle 1000 to orient housing tube 1100 in an orientation configured to cause a curvature of housing tube 1100 within the particular sagittal plane of the inner eye and varying an amount of actuation of actuation mechanism 920. In one or more embodiments, a surgeon may aim optic fiber distal end 1151 at any target within a particular frontal plane of the inner eye by, e.g., varying an amount of actuation of actuation mechanism 920 to orient a line tangent to optic fiber distal end 1151 wherein the line tangent to optic fiber distal end 1151 is within the particular frontal plane of the inner eye and rotating handle 1000. Illustratively, a surgeon may aim optic fiber distal end 1151 at any target located outside of the particular transverse plane, the particular sagittal plane, and the particular frontal plane of the inner eye, e.g., by varying a rotational orientation of handle 1000 and varying an amount of actuation of actuation mechanism 920. In one or more embodiments, a surgeon may aim optic fiber distal end 1151 at any target of a plurality of targets within an eye, e.g., without increasing a length of a portion of a steerable laser probe within the eye. Illustratively, a surgeon may aim optic fiber distal end 1151 at any target of a plurality of targets within an eye, e.g., without decreasing a length of a portion of a steerable laser probe within the eye.

FIGS. 15A and 15B are schematic diagrams illustrating an exploded view of a handle assembly 1500. FIG. 15A illustrates a side view of a handle assembly 1500. In one or more embodiments, a handle assembly 1500 may comprise an outer cylinder 910, an actuation mechanism 920, and a handle base 940. Illustratively, actuation mechanism 920 may comprise an actuation control 930. In one or more embodiments, handle base 940 may comprise an actuation channel 935. Illustratively, actuation mechanism 920 may comprise an actuating chamber 1510. FIG. 15B illustrates a transparent top view of a handle assembly 1500. In one or more embodiments, handle base 940 may comprise one or more static chambers 1520.

FIGS. 16A and 16B are schematic diagrams illustrating a handle 1600. FIG. 16A illustrates a transparent top view of handle 1600. In one or more embodiments, actuation control 930 may be disposed within actuation channel 935. FIG. 16B illustrates a transparent side view of handle 1600. Illustratively, an actuating chamber 1510 may be configured to align with one or more static chambers 1520. In one or more embodiments, one or more static chambers 1520 may be configured to temporarily fix actuation control 930 in a position within actuation channel 935. For example, a first static chamber 1520 may be configured to temporarily fix actuation control 930 in a first position within actuation channel 935, a second static chamber 1520 may be configured to temporarily fix actuation control 930 in a second position within actuation channel 935, a third static chamber 1520 may be configured to temporarily fix actuation control 930 in a third position within actuation channel 935, a forth static chamber 1520 may be configured to temporarily fix actuation control 930 in a forth position within actuation channel 935, etc.

Illustratively, a static chamber 1520 may be configured to interface with actuating chamber 1510, e.g., to temporarily fix actuation control 930 in a position within actuation channel 935. In one or more embodiments, an interface between a static chamber 1520 and actuation chamber 1510 may be configured to align a static chamber 1520 and actuation chamber 1510 wherein a fixation pin may be temporarily disposed within a static chamber 1520 and within actuation chamber 1510. Illustratively, a fixation pin may be temporarily disposed within a static chamber 1520 and within actuation chamber 1510, e.g., by pushing the fixation pin into a static chamber 1520 and into actuation chamber 1510. In one or more embodiments, actuation control 930 may be temporarily fixed in a position within actuation channel 935, e.g., when a fixation pin is disposed within a static chamber 1520 and within actuation chamber 1510. Illustratively, removing a fixation pin from actuation chamber 1510 may be configured to allow actuation control 930 actuate within actuation channel 935. In one or more embodiments, a fixation pin may be removed from actuation chamber 1510, e.g., by pulling the fixation pin out of actuation chamber 1510.

Illustratively, one or more static chambers 1520 may be configured to house one or more magnets. In one or more embodiments, actuation chamber 1510 may be configured to house one or more magnets. Illustratively, one or more magnets may be configured to temporarily fix actuation control 930 in a position within actuation channel 935. In one or more embodiments, one or more magnets may be disposed within a static chamber 1520 wherein one or more magnetic poles of the one or more magnets may be oriented to cause an attractive force between one or more magnets and actuation control 930, e.g., when actuation chamber 1510 is adjacent to a static chamber 1520. Illustratively, one or more magnets may be disposed within actuation chamber 1510 wherein one or more magnetic poles of the one or more magnets may be oriented to cause an attractive force between one or more magnets and a static chamber 1520, e.g., when actuation chamber 1510 is adjacent to a static chamber 1520. In one or more embodiments, one or more magnets may be configured to cause one or more attractive forces configured to temporarily fix actuation control 930 in a position within actuation channel 935. For example, an attractive force configured to temporarily fix actuation control 930 in a position within actuation channel 935 may have a magnitude in the range of 1 to 50 N. However, an attractive force configured to temporarily fix actuation control 930 in a position within actuation channel 935 may have a magnitude less than 1 N or a magnitude greater than 50 N. Illustratively, an application of a force, e.g., a force having a magnitude greater than a magnitude of an attractive force, to actuation control 930 may be configured to actuate actuation control 930 within actuation channel 935.

In one or more embodiments, temporarily fixing actuation control 930 in a position within actuation channel 935 may be configured to temporarily fix housing tube 1100 in a particular curved position. Illustratively, temporarily fixing housing tube 1100 in a particular curved position may be configured to temporarily fix optic fiber 1150 in a particular curved position. In one or more embodiments, a first static chamber 1520 may be configured to temporarily fix housing tube 1100 in a particular curved position wherein optic fiber 1150 may comprise an optic fiber in a first curved position 1310, a second static chamber 1520 may be configured to temporarily fix housing tube 1100 in a particular curved position wherein optic fiber 1150 may comprise an optic fiber in a second curved position 1320, a third static chamber 1520 may be configured to temporarily fix housing tube 1100 in a particular curved position wherein optic fiber 1150 may comprise an optic fiber in a third curved position 1330, a fourth static chamber 1520 may be configured to temporarily fix housing tube 1100 in a particular curved position wherein optic fiber 1150 may comprise an optic fiber in a fourth curved position 1340, etc.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any probe system. Furthermore, while this description has been written in terms of a steerable laser probe, the teachings of the present invention are equally suitable to systems where the functionality of actuation may be employed. Therefore, it is the object of the appended claims to cover all such variations and modifications as come within the true spirit and scope of the invention.

What is claimed is:

1. An instrument comprising:
    a handle having a handle distal end and a handle proximal end;
    a handle base of the handle, the handle base having a handle base distal end, a handle base proximal end, an outer cylinder interface, and a housing tube guide;
    an outer cylinder of the handle, the outer cylinder having an outer cylinder distal end, an outer cylinder proximal end, and a handle base interface, the outer cylinder disposed over a portion of the handle base wherein the outer cylinder distal end is adjacent to the outer cylinder interface and the handle base proximal end is adjacent to the handle base interface;
    an actuation mechanism of the handle, the actuation mechanism having an actuation mechanism distal end, an actuation mechanism proximal end, and a housing tube housing;
    an actuation control of the actuation mechanism;
    a single housing tube having a housing tube distal end and a housing tube proximal end, the housing tube disposed within the housing tube housing and the housing tube guide;
    an optic fiber disposed in an inner bore of the handle and the housing tube, the optic fiber configured to transmit light for performing ophthalmic surgical procedures;
    an actuation chamber of the actuation mechanism;
    a first magnet disposed within the actuation chamber;
    a first static chamber of the handle, the actuation chamber and the first static chamber configured to temporarily fix the actuation control in a first position within an actuation channel of the handle by a first force between one or more magnets wherein temporarily fixing the actuation control in the first position within the actuation channel of the handle is configured to temporarily fix the optic fiber in a first curved position; and
    a second static chamber of the handle, the actuation chamber and the second static chamber configured to temporarily fix the actuation control in a second position within the actuation channel of the handle wherein temporarily fixing the actuation control in the second position within the actuation channel of the handle is configured to temporarily fix the optic fiber in a second curved position.

2. The instrument of claim 1 wherein the second curved position of the optic fiber is at least 45 degrees greater than the first curved position of the optic fiber.

3. The instrument of claim 2 wherein the second curved position of the optic fiber is at least 90 degrees greater than the first curved position of the optic fiber.

4. The instrument of claim 1 further comprising:
    a third static chamber of the handle wherein the actuation chamber and the third static chamber of the handle are configured to temporarily fix the actuation control in a third position within the actuation channel of the handle.

5. The instrument of claim 4 wherein temporarily fixing the actuation control in the third position within the actuation channel of the handle is configured to temporarily fix the optic fiber in a third curved position.

6. The instrument of claim 5 wherein the third curved position of the optic fiber is at least 45 degrees greater than the first curved position of the optic fiber.

7. The instrument of claim 6 wherein the third curved position of the optic fiber is at least 90 degrees greater than the first curved position of the optic fiber.

8. The instrument of claim 5 wherein the third curved position of the optic fiber is at least 45 degrees greater than the second curved position of the optic fiber.

9. The instrument of claim 8 wherein the third curved position of the optic fiber is at least 90 degrees greater than the second curved position of the optic fiber.

10. The instrument of claim 1 wherein an actuation of the actuation control is configured to curve the optic fiber.

11. The instrument of claim 10 wherein the actuation of the actuation control is configured to curve the optic fiber in a particular transverse plane of an inner eye without increasing a length of the instrument within the inner eye and without decreasing the length of the instrument within the inner eye.

12. The instrument of claim 10 wherein the actuation of the actuation control is configured to curve the optic fiber in a particular sagittal plane of an inner eye without increasing a length of the instrument within the inner eye and without decreasing the length of the instrument within the inner eye.

13. The instrument of claim 10 wherein the actuation of the actuation control is configured to curve the optic fiber in a particular frontal plane of an inner eye without increasing a length of the instrument within the inner eye and without decreasing the length of the instrument within the inner eye.

14. The instrument of claim 1 wherein an application of a second force to the actuation control is configured to actuate the actuation control within the actuation channel.

15. The instrument of claim 14 wherein the second force has a second magnitude and the first force has a first magnitude wherein the second magnitude is greater than the first magnitude.

16. The instrument of claim 1 wherein the first force has a magnitude in a range of 1 to 50 N.

17. The instrument of claim 1 wherein the actuation chamber and the first static chamber are configured to temporarily fix the actuation control in the first position within the actuation channel by a fixation pin.

18. The instrument of claim 1 wherein the first force has a magnitude of less than 1 N.

19. The instrument of claim 1 further comprising:
a second magnet disposed in the first static chamber.

20. The instrument of claim 19 further comprising:
a third magnet disposed in the second static chamber.

* * * * *